United States Patent [19]

Kausch et al.

[11] Patent Number: 5,508,164
[45] Date of Patent: Apr. 16, 1996

[54] ISOLATION OF BIOLOGICAL MATERIALS USING MAGNETIC PARTICLES

[75] Inventors: Albert P. Kausch, Stonington, Conn.; Sandya Narayanswami, Irvine, Calif.; Jerry E. Manning, San Clemente, Calif.; Barbara A. Hamkalo, Laguna Beach, Calif.

[73] Assignee: Dekalb Genetics Corporation, Mystic, Conn.

[21] Appl. No.: 146,434

[22] Filed: Oct. 29, 1993

Related U.S. Application Data

[63] Continuation of Ser. No. 605,852, Oct. 29, 1990, abandoned.
[51] Int. Cl.$^6$ ................................. C12Q 1/68; C12Q 1/00
[52] U.S. Cl. ................................. 435/6; 435/820; 435/7.2
[58] Field of Search ................................. 435/172.3, 820, 435/7.2, 6; 536/239, 25.4

[56] References Cited

U.S. PATENT DOCUMENTS

| | | | |
|---|---|---|---|
| 3,970,518 | 7/1976 | Glaever | 435/239 |
| 4,454,234 | 6/1984 | Czerlinski | 436/526 |
| 4,710,472 | 12/1987 | Saur et al. | 435/285 |
| 4,904,391 | 2/1990 | Freeman | 210/695 |

FOREIGN PATENT DOCUMENTS

| | | | |
|---|---|---|---|
| 0240770 | 3/1987 | European Pat. Off. | G01N 33/553 |
| 0339980 | 4/1989 | European Pat. Off. | G01N 33/543 |
| 2832696 | 3/1978 | France | G01N 33/543 |
| WO86/05815 | 10/1986 | WIPO | C12Q 1/68 |
| WO89/04373 | 5/1989 | WIPO | C12Q 1/68 |
| WO90/07380 | 12/1989 | WIPO | |
| WO90/06045 | 6/1990 | WIPO | C12Q 68/04 |

OTHER PUBLICATIONS

Celeda, R. K. A. et al., "Magnetic Separation of Chromosome 1 from human lymphocytes," European Journal of Cell Biology, 51 (Supp. 30):20, Abstract #p. 1.7, 1990.
Franzusoff, et al., "Immuno–Isolation of Sec7p–Coated Transport Vesicles from the Yeast Secretory Pathway," Nature, 355:173–175, 1992.
Liberti and Feeley, "Analytical– and Process–Scale Cell Separation with Bioreceptor Ferrofluids and High–Gradient Magnetic Separation," Cell Separation Science and Technology, Eds., D. S. Kompala and P. Todd, Chapter 17, pp. 268–287, 1990.
Schnell et al., "The Chloroplast Import Receptor Is an Integral Membrane Protein of Chloroplast Envelope Contact Sites," The Journal of Cell Biology, 111:1825–1838, 1990.
Schreier et al., Plant Molecular Biology Manual B5, Eds., S. B. Gelvin & R. A. Schilperpoort, Kluwer Academic Publishers, Dordrecht, 1988, pp. 5–10.
Hutchinson et al., J. Cell. Biol., 95:609–618, 1982.
Cashmore, A., Szabo, L., Timko, M., et al., "Import of Polypeptides into Chloroplasts," Biotechnology, vol. 3 (Sep. 1985), pp. 803–808.
Cooke, H. and Hindley, J., "Cloning of human satellite III DNA: different components are on different chromosomes," Nucleic Acids Research, vol. 6, No. 10 (1979), pp. 3177–3197.
Damha, M., Giannaris, P., and Zabarylo, S., "An improved procedure for derivatization of controlled–pore glass beads for solid–phase oligonucleotide synthesis." Nucleic Acids Research, vol. 18, No. 13 (1990), pp. 3813–3821.
Dudin, G., Cremer, T., Schardin, M., et al., "A method for nucleic acid hybridization to isolated chromosomes in suspension," Human Genetics, vol. 76 (1987), pp. 290–292.
Dudin, G., Steegmayer, E., Vogt, P., et al., "Sorting of chromosomes by magnetic separation," Human Genetics, vol. 80 (1988), pp. 111–116.
Gengenbach, B., Green, C., and Donovan, C., "Inheritance of selected pathotoxin resistance in maize plants regenerated from cell cultures," PNAS (USA), vol. 74, No. 11 (Nov. 1977), pp. 5113–5117.
Gruissem, W., Greenberg, B., Zurawski, G., et al., "Biosynthesis of Chloroplast Transfer RNA in a Spinach Chloroplast Transcription system." Cell, vol. 35 (Dec. 1983), pp. 815–828.
Hibberd, K., Walter, T., Green, C., et al., "Selection and Characterization of a Feedback–Insensitive Tissue Culture of Maize." Planta, vol. 148 (1980), pp. 183–187.
Howell, K., Gruenberg, J., Ito, A., et al., "Immuno–Isolation of Subcellular Components." in: Morre, D., et al. (eds), Cell–Free Analysis of Membrane Traffic (New York, Liss, 1988), pp. 77–90.
Hunter, J., Mills, G., and Sturrock, R., "Ferrography—a new method for isolation of particles from biological fluids." Journal of Clinical Pathology, vol. 35 (1982), pp. 689–690.
Kvalheim, G., Fodstad, O., Pihl, A., et al., "Elimination of B–Lymphoma Cells from Human Bone Marrow: Model Experiments Using Monodisperse Magnetic Particles Coated with Primary Monoclonal Antibodies." Cancer Research, vol. 47 (Feb. 1, 1987), pp. 846–851.

(List continued on next page.)

Primary Examiner—Richard A. Schwartz
Assistant Examiner—James Ketter
Attorney, Agent, or Firm—Arnold, White & Durkee

[57] ABSTRACT

A method for the isolation and sorting of biological materials has been developed. Biological material includes chromosomes, segments of chromosomes, cell organelles, or other minute cellular components. The biological material is separated from the cellular milieu, if necessary, and anchored to a support. Example of a support are glass coverslips, glass or polymer beads. The anchoring is by means of a reversible cross-linking system. The supported biological material is then labelled with compositions capable of binding to said material, and with magnetic particles. Examples of the binding material include nucleic acid probes and antibodies. An example of the antibodies would be those directed to histones. Other labels, for example, fluoresceinbiotin-avidin may be used. The material may be released from the support and sorted by a magnetic force. This method is an alternative to flow cytometry and presents numerous advantages in terms of time, resolution, purity, and preservation of the structure of the biological material during isolation and separation.

31 Claims, 16 Drawing Sheets

OTHER PUBLICATIONS

Lea, T., Vartdal, F., Davies, C., et al., "Magnetic Monosized Polymer Particles for Fast and Specific Fractionation of Human Mononuclear Cells." *Scand. J. Immunol.*, vol. 22 (1985), pp. 207–216.

Lehmann, J., "Brave New Biosensors." *Biotechnology*, vol. 8 (Aug. 1990), pp. 729–731.

Manning, J., Hershey, N., Broker, T., et al., "A New Method of in situ Hybridization." *Chromosoma* (Berl.), vol. 55 (1975), pp. 107–117.

Margel, S., Beitler, U., and Ofarim, M., "Polyacrolein Microspheres as a New Tool in Cell Biology," *J. Cell Sci.*, vol. 56 (1982), pp. 157–175.

Margel, S., Zisblatt, S., and Rembaum, A., "Polyglutaraldehyde: A New Reagent for Coupling Proteins to Microspheres and for Labeling Cell–Surface Receptors. II. Simplified Labeling Method by Means of Non–Magnetic and Magnetic Polyglutaraldehyde Microspheres." *Journal of Immunological Methods*, vol. 28 (1979), pp. 341–353.

Menz, E., Havelick, J., Groman, E., et al., "Magnetic affinity chromatography: An emerging technique." *American Biotechnology Laboratory* (Sep./Oct. 1986).

Miltenyi, S., Muller, W., Weichel, W., et al., "High Gradient Magnetic Cell Separation with MACS." *Cytometry*, vol. 11 (1990), pp. 231–238.

Molday, R., Yen, S., and Rembaum, A., "Application of magnetic microspheres in labelling and separation of cells." *Nature*, vol. 268 (Aug. 4, 1977), pp. 437–438.

Morimoto, Y., Okumura, M., Sugibayashi, K., et al., "Biomedical Applications of Magnetic Fluids. II. Preparation and Magnetic Guidance of Magnetic Albumin Microsphere for Site Specific Drug Delivery In Vivo." *J. Pharm. Dyn.*, vol. 4 (1981), pp. 624–631.

Morimoto, Y., Sugibayashi, K., and Akimoto, M., "Magnetic Guidance of Ferro–colloid–entrapped Emulsion for Site-Specific Drug Delivery." *Chem. Pharm. Bull.*, vol. 31, No. 1 (1983), pp. 279–285.

Mosbach, K. and Andersson, L., "Magnetic ferrofluids for preparation of magnetic polymers and their application in affinity chromatography." *Nature*, vol. 270 (Nov. 17, 1977), pp. 259–261.

Mosbach, K. and Schroder, U., "Preparation and Application of Magnetic Polymers for Targeting of Drugs." *Febs Letters*, vol. 102, No. 1 (Jun. 1979), pp. 112–116.

Narayanswami, S. and Hamkalo, B., "High Resolution Mapping of Xenopus laevis 5S and Ribosomal RNA Genes by EM In Situ Hybridization." *Cytometry*, vol. 11 (1990), pp. 144–152.

Narayanswami, S., Kausch, A., and Hamkalo, B., "Reversible Immobilization of In–Situ Hybridized Chromosomes. A New Approach to Chromosome Sorting." (1990), 4th Intl. Workshop on Mouse Genome Mapping, Annapolis, Md. Nov. 4–8 (Abstract).

Padmanabhan, R., Corsico, C., Howard, T., et al., "Purification of Transiently Transfected Cells by Magnetic Affinity Cell Sorting." *Analytical Biochemistry, vol. 170 (1988), pp. 341–348.*

Pain, D., Kanwar, Y., and Blobel, G., "Identification of a receptor for protein import into chloroplasts and its localization to envelopes contact zones." *Nature*, vol. 331 (Jan. 21, 1988), pp. 232–37.

Rembaum, A., and Dreyer, W., "Immunomicrospheres: Reagents for Cell Labeling and Separation." *Science*, vol. 208 (Apr. 25, 1980), pp. 364–368.

Richa, J. and Lo, C., "Introduction of Human DNA into Mouse Eggs by Injection of Dissected Chromosome Fragments." *Science*, vol. 245 (Jul. 14, 1989), pp. 175–177.

Schroder, U., Segren, S., Gemmefors, C., et al., "Magnetic Carbohydrate nanoparticles for affinity cell separation." *Journal of Immunological Methods*, vol. 93 (1986), pp. 45–53.

Senyei, A. and Widder, K., "Drug Targeting: Magnetically Resposive albumin Microspheres—A Review of the system to Date," *Gynecologic Oncology.* vol. 12 (1981), pp. 1–13.

Senyei, A., Widder, K., and Czerlinski, G., "Magnetic guidance of drug–carring microspheres." *J. Appl. Phys.*, vol. 49, No. 6 (Jun. 1978), pp. 3578–3583.

Spangrude, G., Heimfeld, S., and Weissman, I., "Purification and Characterization of Mouse Hematopoietic Stem Cells." *Science*, vol. 241 (1988), pp. 58–62.

Staros, J., "N–Hydroxysulfosuccinimide Active Esters: Bis-(N–hydroxysulfosuccinimide) Esters of Two Dicarboxylic Acids Are Hydrophilic, Membrane–Impermeant, Protein Cross–Linkers." *Biochemistry*, vol. 21 (1982), pp. 3950–3955.

Uhlen, M., "Magnetic separation of DNA." *Nature*, vol. 340 (Aug. 31, 1989), pp. 733–734.

Viegas–Pequignot, E., Dutrillaux, B., Magdelenat, H., et al., "Mapping of single–copy DNA sequences on human chromosomes by in situ hybridization with biotinylated probe: Enhancement of detection sensitivity by intensified–fluorescence digital–imaging microscopy." *PNAS* (USA), vol. 86 (Jan. 1989), pp. 582–586.

Waye, J., Durfy, S., Pinkel, D., et al., "Chromosome-Specific Alpha Satellite DNA from Human Chromosome 1: Hierarchical Structure and Genomic Organization of a Polymorphic Domain Spanning Several Hundred Kilobase Pairs of Centromeric DNA." *Genomics*, vol. 1 (1987), pp. 43–51.

Widder, K., Senyei, A., Burchette, J., et al., "A Rapid Method for Immunofluorescent Staining of Paraffin Sections Using Iron–containing Protein A Microspheres." *Journal of Histochemistry and Cytochemistry*, vol. 29, No. 7 (1981), pp. 870–873.

Widder, K., Senyei, A., and Ranney, D., "Magnetically Responsive Microspheres and Other Carriers for the Biophysical Targeting of Antitumor Agents." *Advances in Pharmacology and Chemotherapy*, vol. 16 (1979), pp. 213–271.

Widder, K., Senyei, A., and Scarpelli, D., "Magnetic Microspheres: A Model System for Site Specific Drug Delivery in Vivo." *Proceedings of the Society for Experimental Biology and Medicine*, vol. 58 (1978), pp. 141–146.

Wu, D. and Walters, R., "protein Immobilization on Silica Supports: A Ligand Density Study." *Journal of Chromatography*, vol. 458 (1988), pp. 169–174.

Narayananswami, S., Lundgren, K., and Hamkalo, B., "Deoxyribonucleic Acid Sequence Mapping on Metaphase Chromosomes by Immunoelectron Microscopy." *Scanning Microscopy Supplement*, vol. 3 (1989), pp. 65–76.

ISOLATION OF BIOLOGICAL MATERIALS USING MAGNETIC PARTICLES

The government may own certain rights in the present invention pursuant to grant number NIH GM 23241.

This application is a Continuation of application Ser. No. 07/605,852, filed on Oct. 29, 1990, now abandoned, entitled ISOLATION OF BIOLOGICAL MATERIALS USING MAGNETIC PARTICLES.

BACKGROUND OF THE INVENTION

1. Field of the Invention

This invention relates to methods and compositions for separating and isolating biological materials by means of magnetic labelling. The material to be labelled is reversibly anchored to a support before being labelled. The magnetic labels contemplated are small enough to be appropriate for use in separating and isolating biological material in the microscopic range, e.g. chromosomes, mitochondria, chloroplasts, and Golgi apparatus. Binding compositions such as nucleic acid probes or antibodies form part of the labelling complex. After release from the support, the labelled material is isolated by sorting in a magnetic field.

2. Description of the Related Art

Biological material is a stew of heterogeneous ingredients, which needs to be separated into component parts prior to many investigations and procedures. The separation methods vary depending on the absolute and relative sizes of the material to be separated, and the degree of purity which must be achieved. To separate relatively large materials, that is, the "meat" of the stew, centrifugation, filtering and density gradient sedimentation are some of the relatively crude methods that are appropriate. To separate small, minute cellular components, the "spices", e.g., chromosomes, flow cytometry has been a major method. Some materials, e.g., the Golgi apparatus, have not been satisfactorily separated by any means as an individual, intact cellular component.

Although there are many variations on the flow cytometry theme, the basic principle of this method is to label the cellular material, for example, chromosomes, according to its DNA content, which will be generally correlated with size, and to separate the material into collecting tubes by laser beams that quantitatively measure the DNA content. Flow separation of human chromosomes has been somewhat successful in completely separating some of the 23 pairs of chromosomes but has resulted in some aggregation of chromosomes of similar sizes, e.g., the human chromosomes 21–22 and Y. Therefore, this method is of limited usefulness. Present methods for separation of small biological materials, e.g., chromosomes, which are in the range of 0.2 to 10 microns or even smaller entities such as B-chromosomes, minichromosomes and double-minute chromosomes, are inadequate or unavailable. Flow cytometry is not sensitive enough to guarantee separation of small individual components which often sort with the debris. Somatic cell methods (hybridization, microcell fusion) can isolate chromosomes but the methods are laborious and unpredictable. What is needed is some kind of separation method that is not solely dependent on size differences, but is related to other inherent properties of the materials to be separated.

A. Chromosome Isolation and Sorting

Cellular components which are major targets for methods of separation and isolation are chromosomes. It is important to be able to analyze the chromosomal composition of a cell, cell line, tissue or organism, because deviations from the correct number of chromosomes usually produce phenotypic abnormalities. The phenotype results from the interaction of the genetic complement and the environment. Structural chromosomal aberrations may also produce abnormalities, if the genetic balance is disrupted. Chromosomal aberrations may be detected by standard karyotyping, wherein photomicrographs of the chromosomes in individual cells are analyzed. Another method of detection is to sort chromosomes from large numbers of cells, by flow cytometry (Gray, 1990) and to compare the results with a standard pattern.

For other purposes, it is also desirable to isolate groups of identical chromosomes. For example, in humans, aneuploidy of chromosome 21[1] is responsible for Down syndrome. To study the properties of this clinically important chromosome, it is helpful to separate large numbers of No. 21 chromosomes from the others, or to isolate individual No. 21's in a background of chromosomes from another species. The former may also be achieved by flow cytometry, the latter by somatic cell hybridization techniques, for example. Although somewhat useful, current techniques for chromosome isolation and sorting each have serious limitations in terms of time and cost, unpredictability, inaccuracies due to contamination, and destruction or alteration of the chromosomes during processing.

[1] Chromosomes are conventionally numbered, usually in decreasing order according to size as determined microscopically at metaphase.

B. Flow Cytometry

Flow cytometry techniques are used for both analysis and sorting of biological macromolecules and cells (Darzynkiewicz and Crissman, 1990).

Flow cytometry currently is the primary method for the purification of specific chromosomes. However, its efficacy is limited by the amount of time (hours or even days) required to sort large quantities of a single chromosome. Furthermore, it is not yet possible to reliably separate different chromosomes whose DNA contents are similar. There is some cross-contamination of chromosomes having similar sizes. Furthermore, it is impossible to separate individual chromosomes by DNA content alone in species such as the mouse whose karyotype consists of similarly sized telocentric chromosomes (these are chromosomes with their primary constrictions, the centromeres, located at one end). In such cases, either somatic cell hybridization, a method whereby a given chromosome may be laboriously isolated in a genetically different background by cell fusion and selection, or a cell type with a non-uniform karyotype, such as is found in mouse strains carrying single Robertsonian translocation chromosomes, which are of a different size and arm-ratio from the nontranslocated chromosomes, may be employed.

The ability to isolate and sort specific chromosomes is of use in the study of both normal and malignant cell processes, and is an essential first step in the creation of chromosome-specific libraries for cloning. For instance, flow sorting of specific chromosomes has been used to detect deletions in apparently balanced translocation chromosomes (Cooke, et al., 1989). Because the deleted translocation is not the quantitative sum of its component parts, the missing part may be deduced. Flow cytometry has also been used to investigate genetic changes associated with the malignant state, as exemplified in a case of familial renal carcinoma, where two oncogenes have been translocated to the derivative chromosomes of a cancer-related translocation (Harris, et al., 1986), a change that is detectable quantitatively.

Although some success has occurred with previous isolation and sorting methods, these are still laborious and inaccurate. Finally, debris and cross-contamination in flow-sorted preparations compromise the utility of this approach. Thus, a method to reliably generate single chromosome preparations in a short time would have many applications in library construction, cloning, and the analysis of genetic changes such as those that occur in cancer.

C. In-Situ Hybridization

In-situ hybridization of middle or high repeat DNA sequences using radioactive probes has been available to those skilled in the art for a long time (Pardue and Gall, 1970). More recently, labelling with non-radioactive probes has been favored to detect the location of the hybridized probe. Hybridization occurs between complementary nucleic acid sequences if conditions are appropriate. As is well known to those skilled in the art, the hybridization conditions, i.e., "stringency," may be controlled to permit hybridizing between segments of various per cent complementarity. Hybridization may occur between probes and segments of different sizes, for example, from high or middle repeat sequences, to single copy DNA. Hybridization may occur between probes and any cellular component containing nucleic acid. Chromosome-specific, repetitive sequence hybridization probes exist (Moyzis, et al., 1987).

Fluorescent rather than radioactive probes are also available, but there are problems in the detection of the fluorescent signal for single-copy DNA sequences because of the weak signal from a small target. Methods for amplification of the signal have been explored, e.g. by enhancing the strength of the signal itself, and are well known to those skilled in the art. Enhancing the signal detection (e.g., by digital image enhancement, Viegas-Pequignot, et al., 1989) is another approach.

There have been attempts to conduct in-situ hybridizations on whole chromosomes in suspension. Success in this venture would facilitate the Fluorescence Activated Cell Sorter (FACS) process for chromosome sorting.

Manning, et al. (1975) reported a scanning electron microscope in-situ hybridization method based on avidin-polymer spheres binding to biotin-coupled nucleic acid probes hybridized to polytene chromosomes.

Dudin, et al., (1988) carried out in-situ hybridization on suspensions of chromosomes prepared as for flow cytometry. Human genomic DNA biotinylated by nick translation was used to label human chromosomes by in-situ hybridization in suspension. The authors stated that streptavidin was covalently coupled to the surface of magnetic beads and these were incubated with the hybridized chromosomes. The human chromosomes from Chinese hamster X human hybrid cell lines were bound to the magnetic beads through the biotin-streptavidin complex and separated from nonlabelled Chinese hamster chromosomes by a simple permanent magnet. Hybridization was visualized by additional binding of avidin-FITC (fluorescein) to the unoccupied biotinylated human DNA bound to the human chromosomes. Large magnetic beads (4 μm) were used in these experiments.

These authors noted that for high purity sorting of chromosomes, the heterogeneous aggregates, in this case hamster mixed with human chromosomes, and interphase nuclei, must be significantly reduced or eliminated. They suggested 1 g sedimentation preferably prior to magnetic separation as a means of solving these problems. Another problem these investigators encountered was severe clumping when large numbers of chromosomes/magnetic beads were used. Overall, this approach has not been very successful due to problems with adventitiously adsorbed contaminants, and chromosome aggregation and loss in the centrifugation steps required for changing solutions during the procedure. Furthermore, buffer components such as hexylene glycol used in preparing chromosome suspensions cause excessive condensation of the chromosome and consequently a loss of accessibility of sequences within the structure of the condensed chromosome. This reduction in sensitivity is obviously detrimental to sequence detection. In addition, the large magnetic particles used which are about the size of some chromosomes in metaphase (~3–4μ) reduce yield because there is a low efficiency of labelling, probably due to limited target accessibility. Finally, lack of reproducibility means that suspension in-situ hybridization cannot be a solution to the problems of flow sorting of chromosomes.

D. Use of Magnetic Systems

Large paramagnetic particles are currently being used in conjunction with DNA diagnostics and cell separations (Kvalhelm, et al., 1987). Magnetic affinity chromatography has also recently become a viable alternative method of purifying biological structures (Menz, et al., 1986). Magnetic solid supports with specific affinity couples are used for separating cells, cell organelles, and microorganisms (see introduction in Dudin, et al., 1988). One member of the affinity couple is usually an antibody covalently bound or physically absorbed to magnetic microspheres. Some of those used are polystyrene beads containing ferric oxide ($Fe_3O_4$) particles (see reviews by Lea, et al., 1985; Howell, et al., 1988).

Magnetic beads were originally developed for immunoassays. They have also been used to separate DNA and RNA (Uhlen, 1989). Some of the original magnetic particles, made by the polymerization of acrylamide and agarose with paramagnetic materials, were heterogeneous in size and magnetic content. Hydrophilic beads have now been developed that are more homogenous in size, density and amount of magnetized material. Such beads sediment homogeneously in magnetic fields. The chemical structure of the particle surface may be varied, providing a flexible system for the attachment of biomolecules.

A magnetic cell sorting system for separation of large numbers of cells according to specific cell surface markers was reported by Miltenyi, et al. (1990). Cells were labelled sequentially with biotinylated antibodies, fluorochrome-conjugated avidin, and superparamagnetic biotinylated microparticles. These cells were then separated on high gradient magnetic (HGM) columns. Retained cells were then eluted from the column. This method was said to be compatible with analysis of separated cells by fluorescent microscopy or flow cytometry (FACS). Miltenyi, et al. (1990) have implemented a suggestion by Molday and Molday to combine small superparamagnetic microparticles and high gradient magnetic (HGM) fields to separate cells; they call this MACS.

E. Reversible Immobilization

Recently, various methods have been developed for the immobilization of biological structures. These have found numerous applications in molecular biology, for instance. Biologically active structures such as enzymes have immobilized on matrices such as silica for use in studies of biochemical catalysis (Wu and Walters, 1988). Oligonucleotides are currently synthesized on controlled pore glass supports (Damha, et al., 1990). Various purification methods and DNA capture methods rely on the immobilization of molecules of interest on a solid support (Bebee and Gebeyehu, 1990). Biosensors and monitoring systems have also been designed using immobilized biomolecules (Lehman, 1990).

Immobilization methods can utilize a variety of chemical crosslinking agents (Staros, 1982), both cleavable and non-cleavable. Thus, immobilization can be reversible or not, as required. However, these methods have not been applied to isolating and sorting of small biological materials. The combination of methods in the present invention addresses the separation and isolation of small biological materials.

SUMMARY OF THE INVENTION

This invention relates to a method for the separation and isolation of a biological material. The general steps in this method are anchoring the biological material to a support to immobilize it, and labelling the biological material with a binding composition which is capable of binding to it. The purpose of the labelling is to take advantage of inherent differences in the biological material with regard to complexing with the binding material, to subsequently form the basis for separation. The biological material-binding composition also is attached to magnetic particles. These magnetized complexes may then be separated in a magnetic field.

More specifically, the invention described herein relates to methods of separating and isolating small biological materials. This is achieved by: 1) reversible immobilization of biological materials, such as chromosomes or segments thereof, B-chromosomes, mitochondria, chloroplasts, and Golgi apparatus, followed by labelling of these structures either with nucleic acid probes complementary to DNA or RNA within the material, or with antibodies, for example, to proteins within the materials or exposed on their surfaces; 2) combining the labelled materials with magnetic particle labels; and 3) isolating individual components or classes of components of the biological material by reversal of the immobilization step and exposure to a magnetic field. An important and unique aspect of this invention is that materials are labelled while they are anchored to a solid support, and then released to facilitate sorting. Another aspect is that the magnetic particles used are small relative to the biological material so that steric hindrance is not a problem, cross-aggregation is minimized, the structure of the biological material is preserved, and resolution of the signal/target is improved.

The biological material is affixed, immobilized or anchored to a support. Any solid support which does not adversely affect the integrity of the affixed material, which is capable of linking to a chemical cross-linking agent, and which may be manipulated to achieve the eventual separation of the biological material, is useful for purposes of this invention. Preferred embodiments of the support are glass, either in the form of coverslips or controlled pore glass beads, or polymer beads. These supports may be scaled up by use of large sheets of similar materials.

The methods of this invention are applicable to any biological material, although they are most advantageous for small cellular components and molecules. Examples of these are chromosomes or segments thereof, double minute chromosomes, cell organelles, such as mitochondria, intact nuclei, chloroplasts, and cell structures such as the Golgi apparatus, synaptonemal complexes, microtubule organizing centers, vacuoles, and the like.

The Golgi apparatus is a cellular organelle that is part of the cytoplasmic membrane system. The Golgi apparatus has a structure of stacked cisternae, and functions in secretory processes.

Double minute chromosomes are dot-like structures as observed under the light microscope. These are observed in cells after exposure to chemical agents, for example, drugs and chemotherapeutic agents. They appear to result from cellular response to such stresses, and are correlated with gene amplification, the production of many copies of a single gene within a cell.

The term "chromosome" refers to normal, intact chromosomes, and aberrant chromosomes regardless of whether the aberration was spontaneous or induced by environmental agents and segments or fragments thereof.

Cells from many sources may be used to provide biological materials for this invention. Examples include tumor cells such as HeLa cells, human LAK cells (lymphokine activated killer cells), cells of PHA stimulated human peripheral blood, bone marrow cells, plant callus cells, plant protoplasts, and the like. Cells which are capable of giving rise to large numbers of dividing cells are preferable.

This invention has particular advantages for small biological materials. For example, chromosomes are of approximate size 0.5–10 µm; mitochondria 5–20 µm; chloroplasts 5–100 µm. As will be evident from the subsequent discussion on magnetic particle sizes, an aspect of this invention is to use small magnetic particles as labels, of the order of 50 nm–10 µm, preferably 50 nm–2.0 µm, for labelling these small biological materials. The choice of these small particles improves resolution.

The support to which the biological materials will be anchored is generally treated with a silane, a cleavable cross-linking agent, and a releasing agent. Although treatment of glass surfaces with the homobifunctional cross-linker DTSSP is an embodiment of a method of immobilization, other schemes such as the use of heterobifunctional cross-linkers for reversibly anchoring chromosomes to a solid support are preferred. These include heterobifunctional agents such as SPDP. The use of controlled pore glass (CPG) beads both with and without attached long chain alkylamine linker arms is preferred as a support. The foam-like structure and relatively small amount of available outer surface of the CPG allows the attachment of chromosomes to their surfaces through fewer crosslinks, and hence improves yield after reversal of the linkages. It is also possible to reversibly crosslink isolated chromosomes to polymer beads that have been derivatized with oligopeptides terminating in attackable amino groups. This approach combines solid phase peptide synthesis protocols with the techniques described above, and is attractive because oligopeptides can be custom made with, for example, strong internal rigidity, and to a variety of lengths. Thus, characteristics of such linker molecules for maximal capture of biological material and release after crosslink reversal can be optimized. In addition, the use of microbead supports that can be manipulated in suspension instead of a flat glass surface, may improve efficiency of reactivity.

The efficiency of any reversible immobilization procedure depends on having a controllable reaction with the crosslinking agent. Homobifunctional crosslinkers, for example, DTTSP, are successful for purposes of this invention although prior treatment of supports such as glass has the potential to render a proportion of the linker unavailable for reaction with the biological material due to reaction of both ends with the support. This problem was overcome by the use of heterobifunctional thiol cleavable crosslinkers such as N-succinimidyl 3-(2-pyridyldithio)propionate (SPDP). Use of compounds such as these permits a more controllable, and more effectively reversible immobilization procedure because supports are modified so that they will react with only one end of the crosslinker, leaving the other end free to react with the biological material. An example of a releasing agent is dithiothreitol (DTT), which cleaves disulfide bonds.

The immobilization procedure described above allows efficient labelling of biological materials for separation without the loss and aggregation associated with carrying out labelling reactions in suspension. Furthermore, debris and contaminants can be easily washed away from an immobilized preparation. Reversal of the immobilization step then allows the labelled material to be recovered for sorting.

The anchored biological material is contacted with a composition that will bind to it. The choice of a binding composition will depend on what the sorted material is to be used for. In the case of chromosomes, the goals contemplated include production of chromosome specific libraries, and production of physiologically intact chromosomes.

For the first application, the preferred binding compositions are nucleic acid probes because chromosomal DNA is the target of the isolation procedure. For examples, probes may be to the repetitive sequences of specific centromeric regions, to the entire chromosome, or to single gene copies. In an exemplary embodiment, probes are nick-translated plasmids, usually 500 bp–5 kb in length allowing specific chromosomes to be recovered. In the second application, the preferred binding compositions are antibodies to proteins contained within the chromosomes, e.g., histones (H1), so that intact chromosomes are recovered form a mixture of cell components. Another aspect of this second application is to isolate specific chromosomes on the basis of chromosomal proteins rather than DNA sequences. All these procedures are also applicable to interphase chromosomes, as well as to metaphase chromosomes, and segments of chromosomes. Nucleic acid probes or antibodies to specific proteins, are also useful labels for cell organelles such as mitochondria and chloroplasts, and for other small biological materials.

The binding compositions are generally labelled. In an illustrative embodiment, the label was biotin-avidin with fluorescein. In this case, intensified fluorescent digital-imaging microscopy is employed to detect the fluorescent label (Viegas-Pequignot, et al., 1989).

"Hybridization cocktails," that is, preparations of DNA which hybridize to different portions of the same chromosome may be used to coat an entire chromosome, and to bind magnetic particles, facilitating separation of the labelled from non-labelled chromosomes when a magnetic force is applied. Methods for "painting" entire specific chromosomes to coat them with labelled probes have also been developed. Oncor (Gaithersburg, Md.) sells a centromeric probe cocktail which reportedly detects all human centromeres.

Nick-translated biotinylated DNA probes are used routinely for mapping gene location on chromosomes by non-radioactive in-situ hybridization. The biotinylated probe may be localized by reaction with proteins which have a high affinity for the biotin (for example, avidin, streptavidin, rabbit anti-biotin) and visualized by conjugation to a fluorescent marker, for light microscopy, or colloidal gold, for electron microscopy. Both of these reactions increase the physical surface area of the signal. Commercial colloidal gold (Auroprobe, 10 nm) is capable of adsorbing two streptavidin molecules. Biotinylated ferric oxide particles (Collaborative Research, 1000 nm) may be reacted with the colloidal gold, thereby rendering the chromosomes magnetically responsive proportional to the amount of bound iron. The Km of these reactions ranges from $10^{-12}$ to $10^{-15}$. Magnetic particle sizes should preferably maintain a (–)10 g force attraction to a small rare earth magnet, for example, neodymium-iron-boron.

Naked magnetic (ferric oxide) particles may be purchased from commercial suppliers, for example, 1) Ferro Fluids (Nashua, N.H.); 2) Advanced Magnetics (Collaborative Research, Cambridge, Mass.); and 3) Alfa Particles (Danvers, Mass.). These commercial preparations of naked ferric oxide range in particle and particle aggregate sizes. All these preparations are heterogeneous with regard to particle size and particle aggregate size. To use these preparations for this invention, they must be fractionated into more accurate by defined size classes. In a typical fractionation experiment, a density sedimentation column (1–2 meter) and an electromagnet were used to collect various size classes. The particles were suspended in 100% ethanol to prevent oxidation. A slurry was placed in the column and left for 24 hours. At the end of that time, a gradient had formed—aggregates toward the top, heavy particles to the bottom. Specific magnets could be left against the column at certain size levels, and the other particles rinsed through. Because of the method of collection, these particles were by definition responsive to a magnetic field.

Examination of these particles in the electron microscope after separating them by size revealed the following:

There were two types of particles in the 100–500 nm and the 500–1000 nm size classes: solid single particles and aggregates of much smaller particles (about 10–20 nm). These aggregates appeared as grape-like clusters in the electron microscope. Resedimentation by density sedimentation further separated the aggregates from the solid particles.

One type of material that can be attached to magnetic particles to enhance their versatility, is proteins. Two of the methods used to attach proteins to the ferric oxide particles are: 1) direct adsorption; 2) covalent attachment through a silane. Any protein has the potential to be covalently linked to magnetic particles. A preferred silane is N-(2-aminoethyl)-3-amino proplytrimethoxysilane (Pierce Chemical Co.). This silane provides functional amino groups which may be activated by glutaraldehyde and linked to specific proteins.

Collaborative Research sells magnetic particles with covalently attached antibodies. This company also sells biotinylated particles. Examination of these preparations in the transmission electron microscope (TEM) revealed two classes of particles reminiscent of those described above for the naked ferric oxide preparations, that is, single particles and aggregates (grape-like clusters).

For purposes of this invention, biological materials are preferably labelled with the grape-like ferric oxide aggregates. Because the ferric oxide particles are magnetically responsive, the labelled biologically material is also magnetically responsive.

The smaller magnetic particles such as those produced by Bangs Laboratories (50 nm) have advantages over larger ones. The binding reaction is faster, quantitative differences in labelling are feasible, beads do not interaggregate, and they are easy to sterilize. A disadvantage is that the small magnetic moment increases separation times in magnetic fields of conventional geometries. Regardless, separation using the methods of this invention may be achieved in minutes. Lower magnetic fields provided by commercially available permanent magnets (100–1000 gauss) are adequate to remove materials such as chromosomes from a column. Rare earth magnets are preferred because they have intense magnetic fields (Advanced Magnetics).

An aspect of the invention is to release the labelled biological material from a solid support so that they can be isolated and/or sorted. This process enables the purification of the said material, that is, obtaining suspensions enriched for a particular class of structure, e.g., if the material is chromosomes, a class of No. 21 chromosomes may be recovered. For simple laboratory use, a 10 ml pipette was used as a separation column. A series of magnets were placed on the outside of the pipette and small magnetic particles in a buffer were allowed to fall by gravity through the pipette. These particles attached to the inside of the pipette adjacent to the magnets.

If the materials are to be used in subsequent applications wherein probes and magnetic particles are not desirable, these may be removed from the biological material by phenol extraction, by melting the complexes off with temperatures of about 50° C., detergents, high salt concentration or treatment with a proteolytic enzyme. For instance, papain digestion may be used to cleave antibody hinge regions and so remove iron. Alternatively, other proteases could be used. Any other method to remove the magnetic particles and/or the binding composition and which does not adversely affect the structure of the biological material for subsequent applications is also within the scope of this invention.

More than one probe may be applied to the chromosomes. If all the probes hybridize to the same chromosome, this may enhance sorting by providing a stronger signal. If the probes are to different chromosomes, they must be distinguishable in some way so the chromosomes may be separated by the magnetic field.

To sort more than one chromosome, chromosomes are labelled with differently substituted DNA probes. Each of these is labelled with magnetic particles of different sizes and/or amounts. After detachment, the labelled preparations are exposed to a weak magnet to isolate materials labelled with a large amount of particles, followed by exposure to a strong one, to isolate chromosomes labelled with the smaller particles. A gradient magnetic field may be used for simultaneous separation of differently labelled chromosomes. FACS may be used if chromosomes are labelled with a fluorochrome before cleavage of the cross-linkage. Thus, currently available multiple fluorescent detection methods may be exploited to sort biological material having different labels.

After the biological material is labelled, the linker is cleaved and a magnetic force pulls the magnetic particles and the attached substance to be purified, in illustrative embodiments, chromosomes or small organelles, to the vessel wall or a collecting reservoir. In an illustrative embodiment, the labelled material may be pelleted in microtiter wells and purified from a supernatant by 1 g centrifugation. Unwanted particulate matter remains in suspension or at the bottom of the vessel to be discarded. Magnets such as the Bio Mag separator (Advanced Magnetics, Inc.) provide the force for magnetic separation. There are also flat magnetic separators (Advanced Magnetics) for flat tissue culture vessels.

As mentioned above, biotin-avidin links are one example of a labelling system. The non-covalent biotin-streptavidin interaction is strong and stable ($K_M=10^{-13}$). Methods have been developed for amplifying signals from labelled loci on chromosomes. The goal was to be able to detect the genes in-situ, that is, to determine their chromosomal location. This process using colloidal gold was used for physical mapping of genes on chromosome at the electron microscope level.

Colloidal gold is commonly used in standard electron microscopy in-situ reactions to localize a labelled DNA probe either by antibody coupling reactions or streptavidin-biotin affinity. Colloidal gold is inexpensive and simple to prepare in a variety of sizes; it is extremely electron opaque; and it does not bind adventitiously to chromatin or chromosomes. It may be used with the magnetic particles as a bridge, although it is contemplated as useful only for specific applications, for example, when it is necessary to demonstrate that magnetic beads bind specifically to loci of interest.

The diploid nucleolar organizing region (NOR) of *X. laevis* was used to define the resolution of the labelling procedure. This region contains about 450 copies of the 18S+28S ribosomal RNA genes. In the *X. laevis* cell line XTC, which contains this NOR chromosome in addition to a second NOR some 10–20 times larger, both NOR chromosomes were labelled with magnetic particles. Thus, using the protocols described herein, the nucleic acid-magnetic particle complex is capable of detecting typical middle repeat gene clusters, in addition to typical highly repeated sequences such as mouse centromeric satellite DNA. The resolution of labelling extends to single copy sequences.

The availability of the rapid and effective sorting method of the present invention has many applications. It allows the production of large amounts of pure chromosomes for various purposes, such as library construction and cloning. As such, it facilitates the elucidation of both normal and aberrant cellular processes. The methods of this invention also permit small organelles such as mitochondria, chloroplasts and Golgi apparatus to be sorted for biochemical analysis. Transformation by DNA uptake of these materials into host cells or vectors is also facilitated. Transformation has important applications by transmitting commercially or clinically desirable traits into host cells.

An important aspect of the invention is reversible anchoring to a solid support. This aspect per se has important uses. Reversible immobilization methods for cell organelles may have commercial applications if the biochemical activity of anchored organelles is preserved, i.e., sensor design energy cells, prosthesis design for the replacement of defective organelles (for instance, some neuromuscular diseases are due to defective mitochondria). With appropriate solid supports available, scaling up is also possible. In the case of chromosomes, this system may be considered as a solid phase chromosome system, and as such is amenable to applications other than chromosome sorting. It may be used as a medium for directed chromosome modification, because in essence it allows chromosomes to be subjected to various defined manipulations and then recovered for further analysis. Entire modified chromosomes could, for instance, be used for cell transformation and the introduction of desirable traits, or as a functional assay for DNA sequences of interest in eukaryotes, a need which has not yet been filled in molecular biology and which is of considerable importance. Modified chromosomes could be used for the construction of artificial chromosomes.

BRIEF DESCRIPTION OF THE DRAWINGS

Other objects and advantages of the invention will become apparent upon reading the following detailed description and upon reference to the drawings in which.

Figure 1:
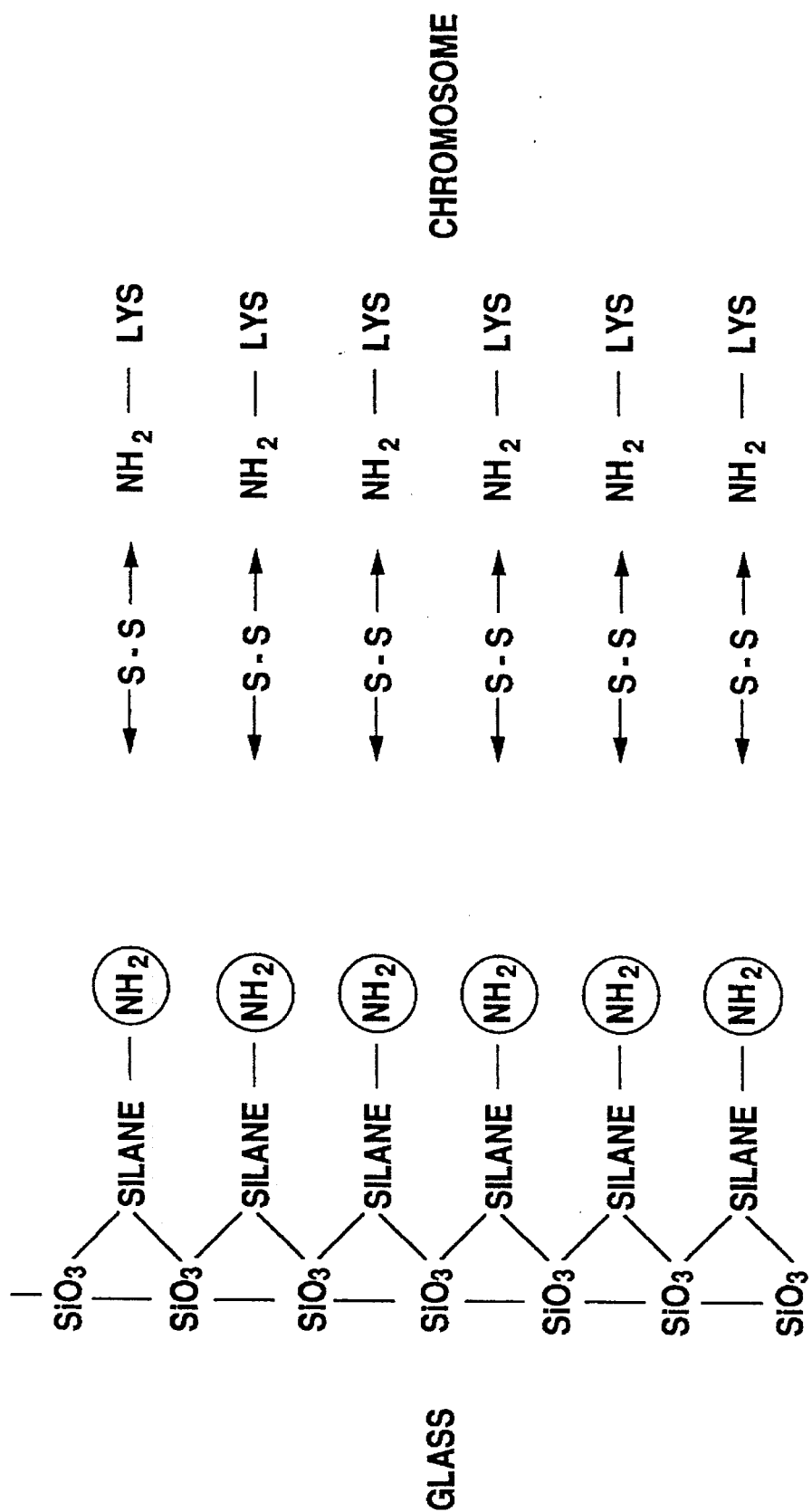
FIG. 1 is a representation of a reversible linkage between a chromosome and a support in the form of a piece of glass, for example, a coverslip.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Techniques originally developed to use nonisotopically labelled probes for in-situ hybridization to localize a variety of sequences to vertebrate metaphase chromosomes at the electron microscope (EM) level (Narayanswami, et al., 1989) were modified for the goals of this invention. This invention combines these techniques with novel approaches to separation and isolation of small biological materials based on reversible immobilization, paramagnetic particle labelling, and separation by magnetic force. Examples of the biological material for which this invention is applicable include chromosomes, segments of chromosomes, mitochondria, chloroplasts, Golgi apparatus, and the like.

The ability to reduce contaminant levels by extensive rinsing of an immobilized preparation is an important advantage over current protocols for in-situ hybridization in suspension. Reversibility of the attachment is another important aspect. The anchoring reduces problems due to internal aggregation of the biological material and other undesirable interactions.

Supports were prepared by treating them with an agent which can anchor chromosomes, segments of chromosomes or small organelles. These materials were attached to derivatized glass surfaces with various reversible cross linkers, carried through an in-situ hybridization reaction, and later released from the support with a strong reducing reagent. (FIGS. 1 and 2).

FIG. 1 is a representation of a reversible linkage between a chromosome and a support in the form of a piece of glass, for example, a coverslip. LYS refers to the free amines ($NH_2$) from the lysine residues in the chromosomes. The S—S link is provided in this representation by DTSSP which recognizes free amines ($NH_2$) at both ends. The silane provides free amines to the glass solid support, shown as a linkage of $SiO_3$.

Figure 2:
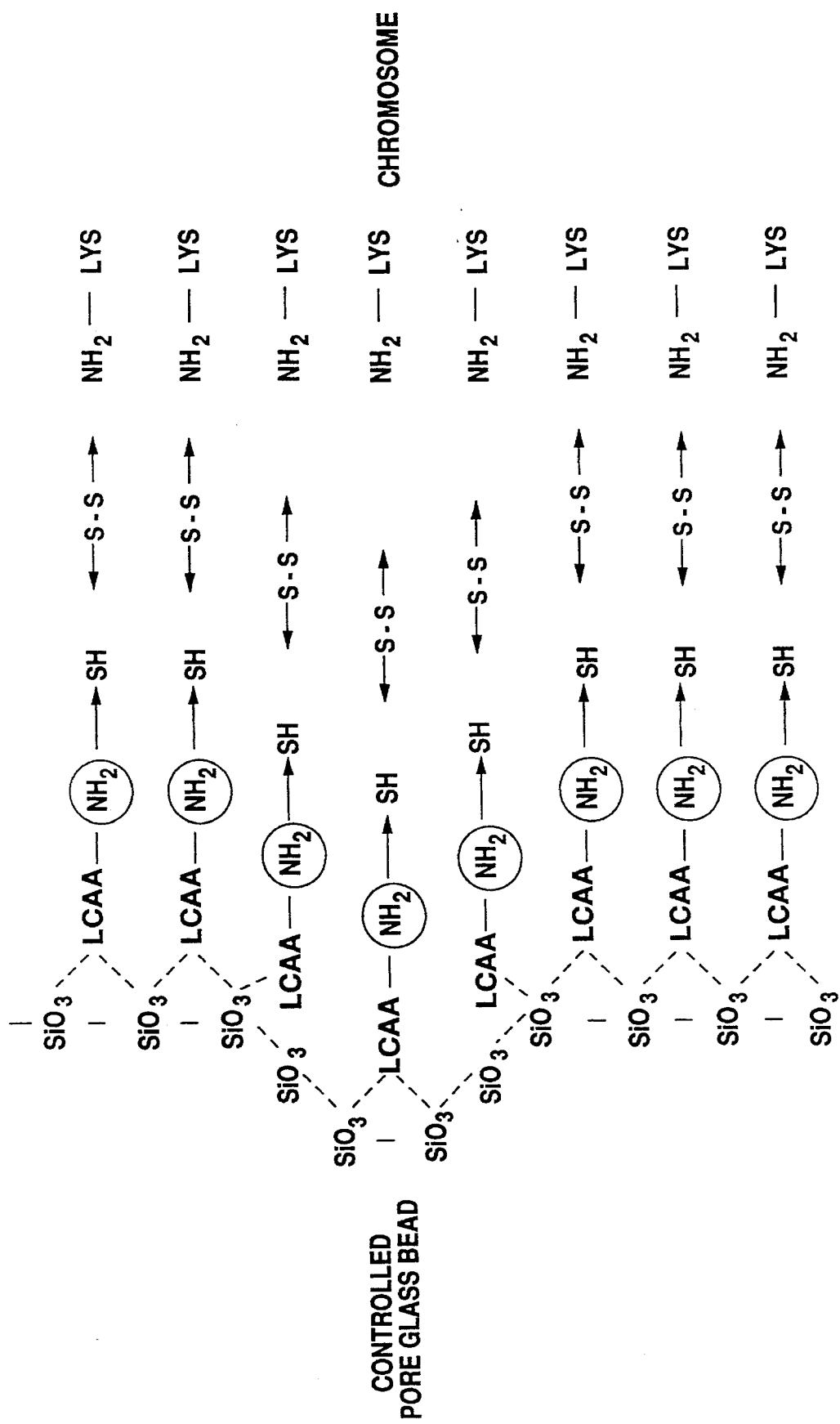
FIG. 2 is a representation of a reversible linkage between a chromosome and a support in the form of a controlled pore glass bead (CPG).

FIG. 2 is a representation of a reversible linkage between a chromosome and a support in the form of a controlled pore glass bead (CPG). LYS refers to free amino groups ($NH_2$) provided by lysine residues in the chromosome. The S—S link is provided in this illustration by SPDP which recognizes the sulfhydryls (SH) on one end and the free amines on the other. This band is cleavable disulfide linkage which may be released with a releasing agent (e.g., 50 mM DTT). The free amine ($NH_2$) is converted to sulfhydryl groups by Traut's reagent. LCAA refers to the long chain alkyl amine which provides free amines on the support phase. The solid support phase of the controlled pore glass bead CPG is shown as a linkage of $SiO_3$.

The reducing reagent does not remove the labelled probes from the reacted biological material. Reversible crosslinkers (DTTSP/SPDP) are used to anchor chromosomes to the glass supports. The anchored chromosomes have to be fixed to protect them against destruction by denaturing agents. A nonreversible crosslinker, such as glutaraldehyde, was generally used as a post-fixative to increase stability of the biological material. It was determined for chromosomes that the number of cross links introduced by post-fixation is directly correlated to maintenance of chromosome integrity throughout this procedure. A titration series may be constructed to optimize time and concentration values for reversible crosslinker and nonreversible post-fixatives for different biological materials.

Figure 3:
FIG. 3 shows a chromosome which has been isolated and released from a glass solid phase support after fixation with 0.1% glutaraldehyde, standard in-situ reaction, and reduction with 50 mm of DTT, a releasing agent.
Figure 4:
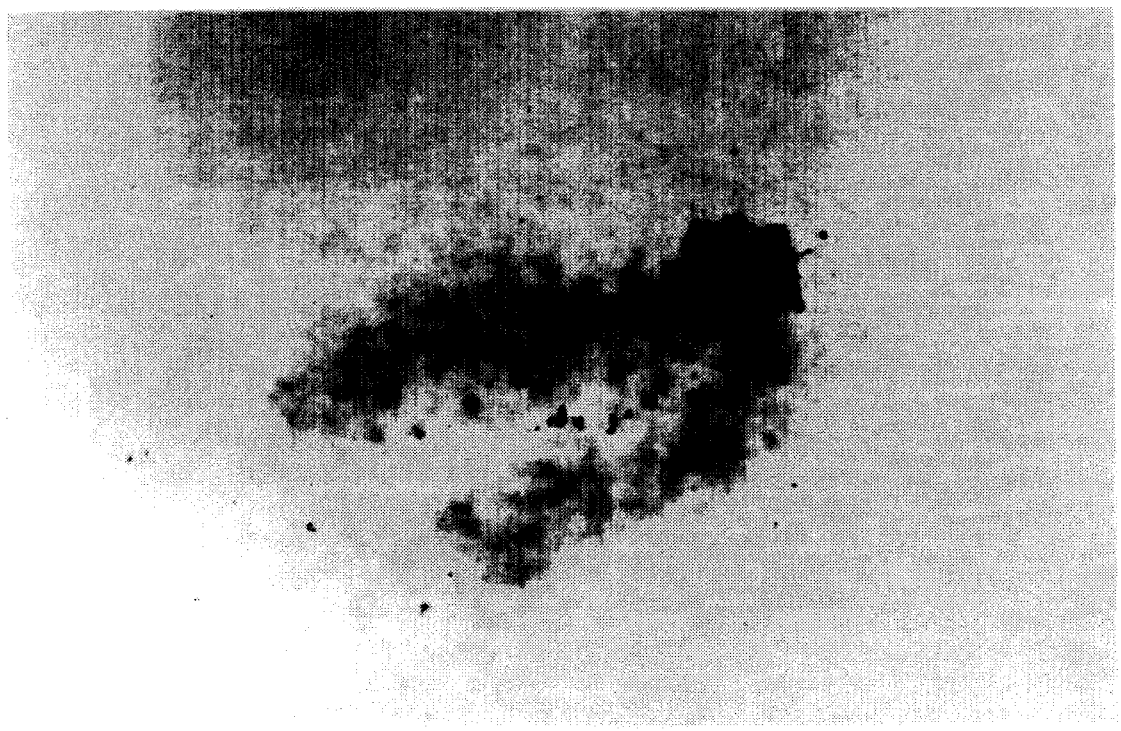
FIG. 4 is the same as FIG. 3 except that fixation was in 0.03% glutaraldehyde.
Figure 5:
FIG. 5 is the same as FIG. 3 except fixation is in 0.01% glutaraldehyde.

FIGS. 3–5 show the morphologies of chromosomes isolated and released from a glass solid phase support, after post-fixation with 0.1%, 0.03%, and 0.01% glutaraldehyde, standard in-situ reaction, and reduction with 50 mm DTT, a releasing agent. Chromosomal morphology was optimal at 0.1% glutaraldehyde post-fixation.

The use of flat glass as a solid support phase for reversible attachment of chromosomes during in-situ hybridization reactions has some limitations for use in chromosome sorting and isolation. Controlled pore glass beads of pore size smaller than chromosomes are preferred so that less of the chromosomal surface area is in contact with the support, reducing the time and concentration of the releasing agent, e.g., DTT, necessary to remove it. The presence of pores may also improve reagent access to crosslinks.

Preparation of the Biological Material

1. Chromosomes

Chromosome preparations were made as described in Narayanswami, et al. (1989) with minor modifications. These methods were in turn modifications of that proposed by Miller (1969). In one embodiment, mouse L929 cells were arrested with 50–80 ng/ml Colcemid (Gibco) overnight. Cells at metaphase of the mitotic cycle were collected by shaking them off the bottom of the culture vessel and lysing them in the presence of 0.5% Nonidet P-40. After 1 min. at room temperature, the chromosome suspension was layered over a cushion of 1M sucrose, at about pH 8.5 in the cap of a 15 ml Falcon tube. The cap contained a glass coverslip that had previously been silanated (see following section) and prefixed with the thiol-cleavable crosslinking agent dithiobis-sulfa succinimidyl propionate (DTTSP). Preparations were centrifuged as described in Narayanswami, et al. (1989). The coverslips were removed from the microcentrifugation chambers, and rinsed briefly in 0.4% Kodak Photoflo 200, at about pH 8.5, followed by about a 5 min. rinse in 2×SSC, 150 mM glycine, to quench the crosslinker. The preparations were kept moist with the solution in use.

2. Cell Organelles

Cell organelles can be isolated by preparing a cell lysate and reacting it to the appropriate cognate antibody immobilized on magnetic particles (i.e., to a chloroplast membrane protein), allowing recovery of the organelle in a magnetic field.

To collect organelles, cells or protoplasts are lysed by physical or isotonic distruption into an isolation buffer which is appropriate for specific organelles and cell types. An example of an appropriate buffer for chloroplast isolation is described by Gruissem, et al. (1983). Crude organellar preparations can be made by differential centrifugation (see Cashmore, et al. (1984)). The crude organellar pellet is then layered over a cushion containing an appropriate percol concentration adjusted for the organelle of interest, in a 15 ml Falcon tube cap. The cap contains a glass coverslip that has been silanated and prefixed with DTTSP, so that following centrifugation the organelles are immobilized to the surface of the glass.

Silanation and Prefixation of Coverslips

In an exemplary embodiment, the supports were coverslips. Acid washed round glass coverslips about 1 mm in diameter were treated with N-(2-aminoethyl)-3-aminopropyl trimethoxysilane (Pierce) in order to attach amino groups to their surfaces (FIG. 1). Coverslips were prefixed in freshly made 1 mM DTSSP (Pierce), 2×SSC for 1 h at room temperature. (See Methods)

Chromosome Immobilization (Anchoring)

In order to reversibly immobilize or anchor biological material, supports were treated with reversible crosslinkers. In an illustrative embodiment, glass surfaces were derivatized with N-(2-aminoethyl)-3-aminopropyl trimethoxysilane, according to specification by Pierce Chemical Co. Silane provides functional amino groups that can be attacked by the thiol cleavable crosslinking agent dithiobis-sulfo succinimidyl propionate (DTTSP). (Staros, 1982) (FIG. 1). Chromosomes from cell lysates were pelleted through sucrose by standard methods (Rattner and Hamkalo, 1978) and attached to these prepared surfaces by reaction of the amino groups of chromosomal proteins with bound DTSSP. Although postfixation with glutaraldehyde was necessary to stabilize the chromosomes against degradation, in-situ hybridization reactions were conducted on these preparations using biotinylated probes (FIG. 6), and target sequences were detected by standard antibody sandwich amplification schemes (Narayanswami, et al., 1989) followed by either colloidal gold (for electron microscopy) (FIG. 7), or magnetically responsive biotinylated ferric oxide particles (FIG. 8) for sorting in a magnetic field. The signal was amplified (FIG. 9).

Figure 6:
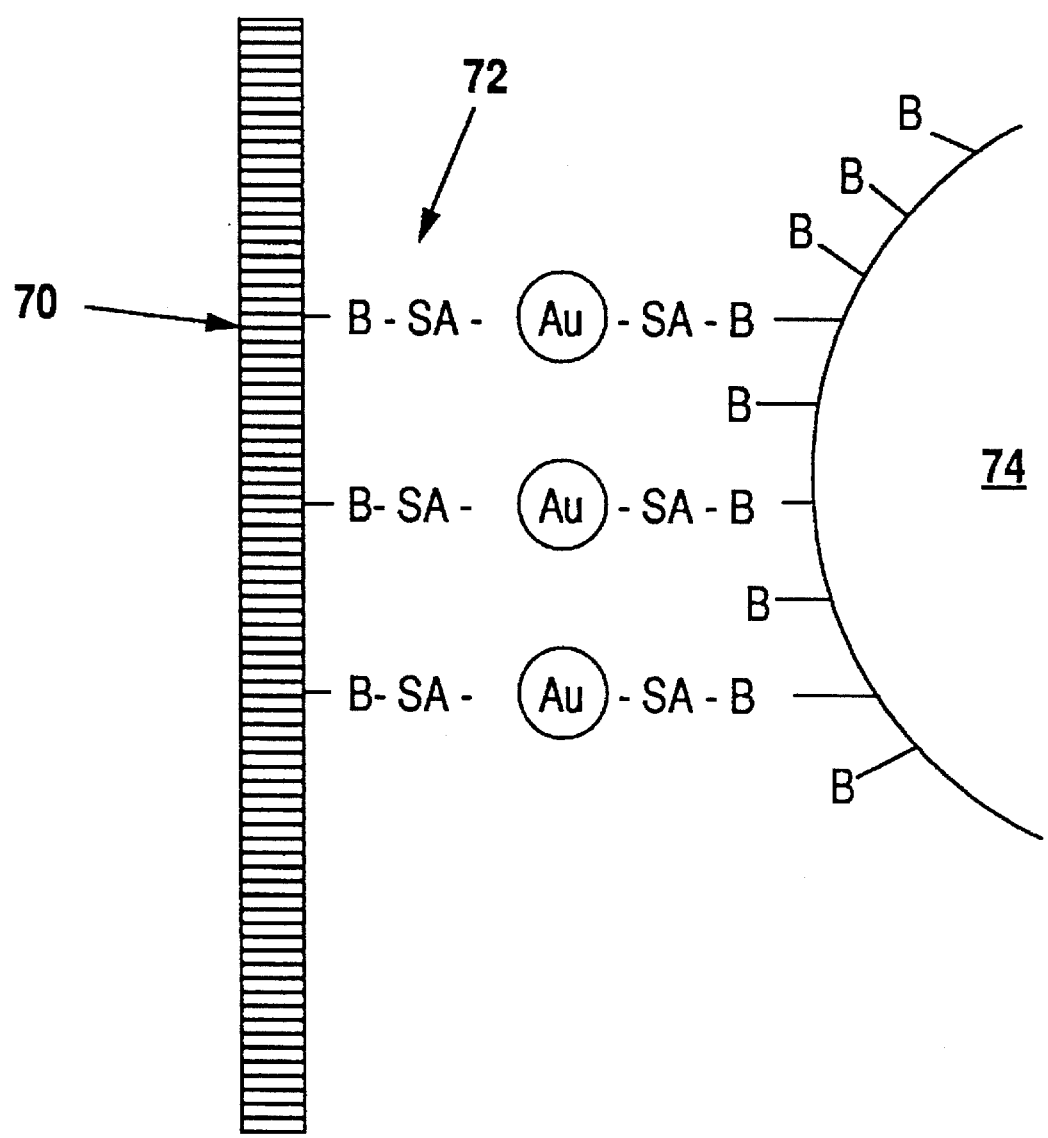
FIG. 6 is a diagrammatic representation of linkage between chromosomal DNA and ferric oxide (1000 nm) via a biotinylated, DNA probe, streptavidin, and colloidal gold.

FIG. 6 is a diagrammatic representation of linkage between chromosomal DNA 70 and ferric oxide 74 (1000 nm) via a biotinylated (B) DNA probe 72, streptavidin (SA) and colloidal gold (Au). The Km of these reactions ranges from $10^{-12}$ to $10^{-15}$.

Figure 7:
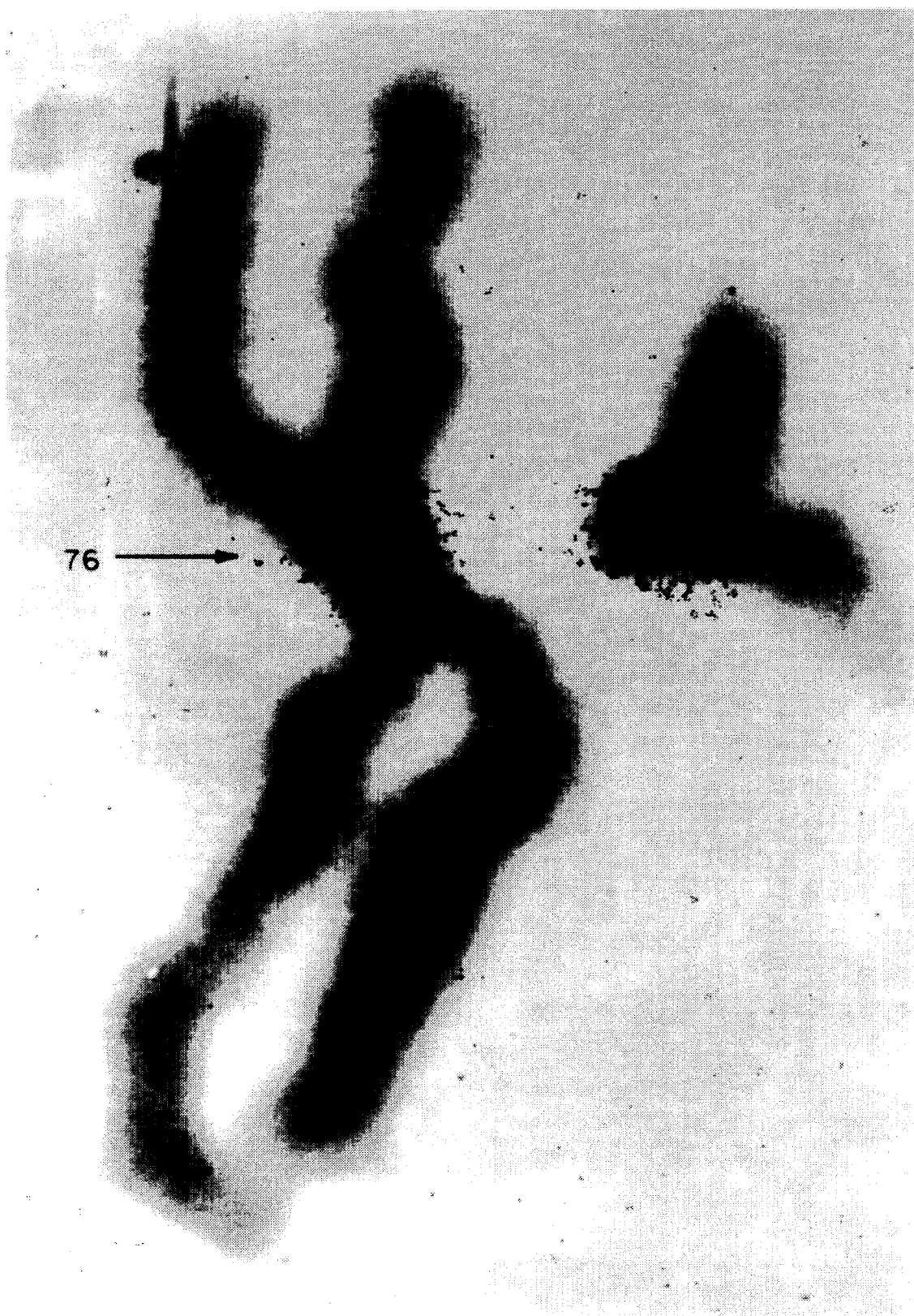
FIG. 7 shows a chromosome labelled with colloidal gold (see Reaction 1 in Table 1 of Example 1, described hereinafter).

FIG. 7 shows a chromosome labelled with colloidal gold (see Reaction 1 in Table 1 of Example 1, described hereinafter). The label 76 can be seen at the centromeric region (the centromere is the primary constriction of each chromosome). This position is consistent with the hybridization characteristics of the nucleic acid probe.

Figure 8:
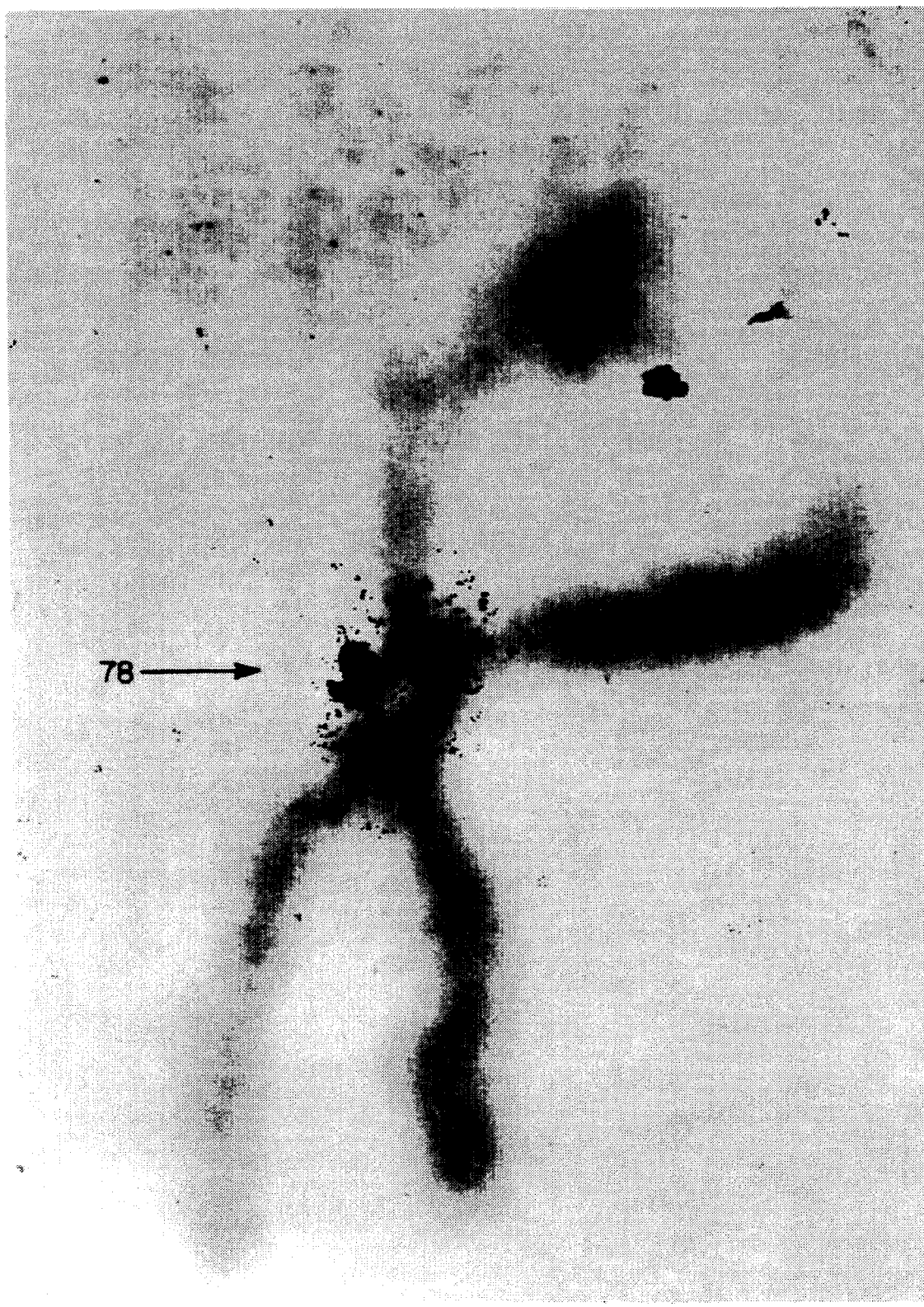
FIG. 8 shows a chromosome in which iron oxide particles are bound to the colloidal gold as illustrated in FIG. 7 (see Reaction 2 in Table 1).
Figure 9:
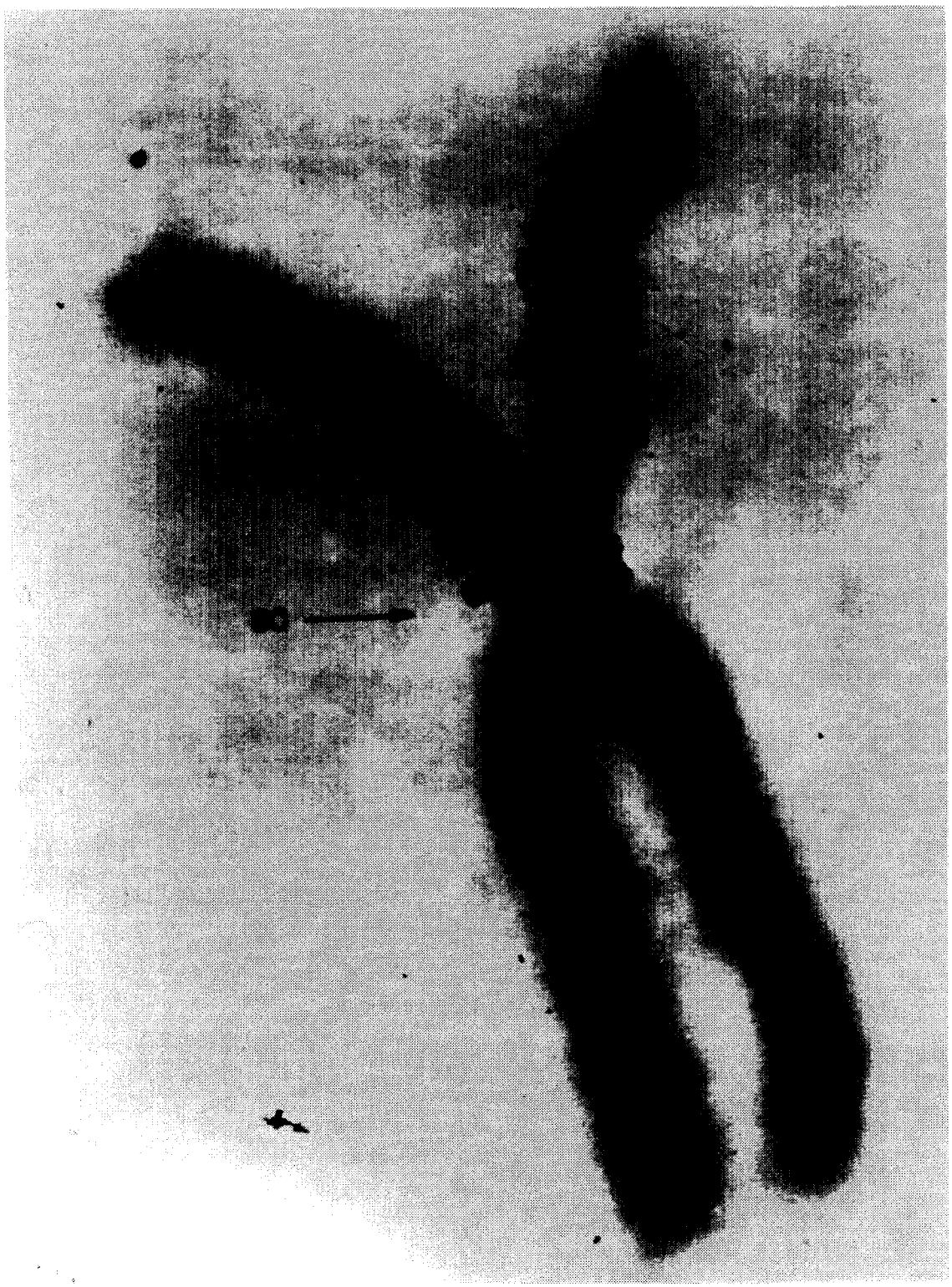
FIG. 9 shows a chromosome in which the signal has been amplified.
Figure 10B:
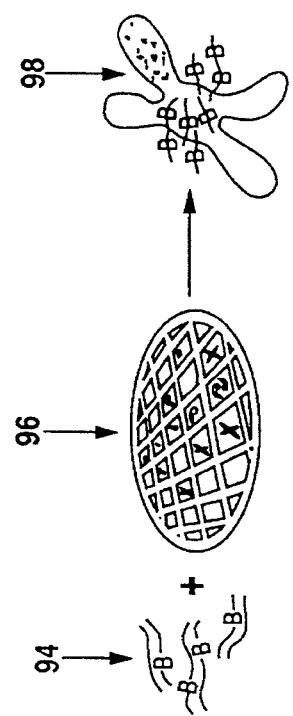
FIG. 10 is a schematic representation of in-situ hybridization of electron micrograph chromosome preparations.
Figure 10D:
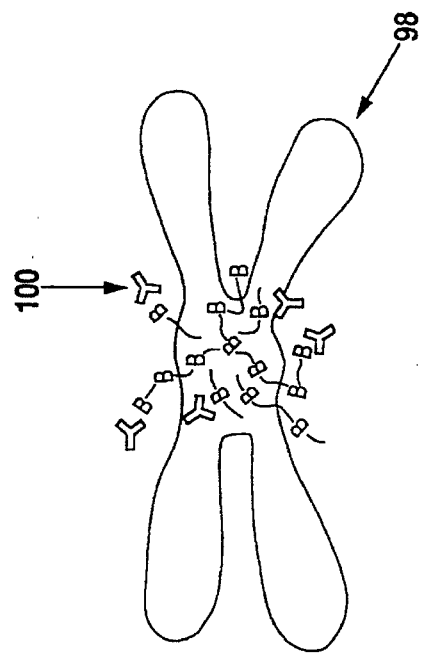
Figure 10A:
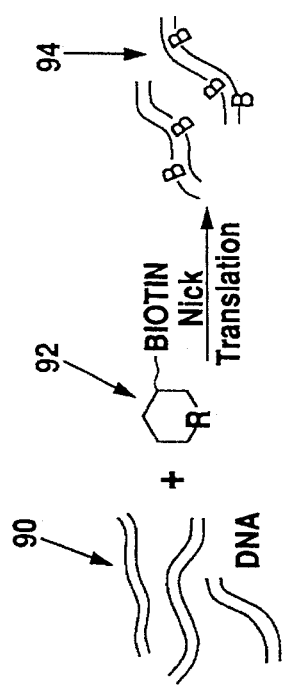
Figure 10C:
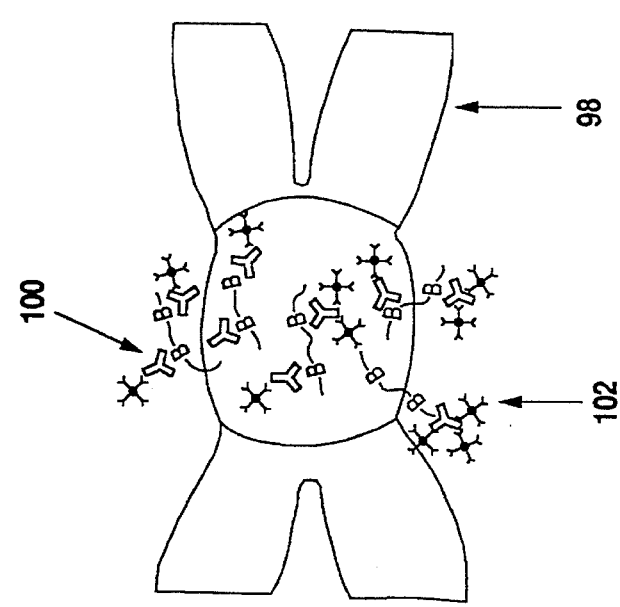

FIG. 8 shows a chromosome in which iron oxide particles are bound to the colloidal gold 78 as illustrated in FIG. 7 (see Reaction 2 in Table 1).

FIG. 9 shows a chromosome in which the signal has been amplified 80. A positive reaction is evidenced by a deposition of product at the centromeric region. This Reaction (see 4 in Table 1) addressed the question of steric hindrance.

Labelled chromosomes were released from the solid surface by incubation with 50 mM DTT, which cleaves the disulfide linkage present in the crosslinker, and electron microscopy revealed that they are both morphologically intact and specifically labelled. Ferric oxide labelled chromosomes were then sorted in a magnetic field. These mechanisms are shown schematically in FIG. 10, a schematic representation of in-situ hybridization of electron micrograph chromosome preparations. Whole mount metaphase chromosomes were hybridized with a biotinylated DNA probe 92. Detection of the probe was with a primary antibiotin antibody 100, followed by a secondary antibody coupled to colloidal gold or magnetic particles 102. Mouse satellite DNA 90 was nick translated with biotin-dUTP 92 to yield labelled DNA 94. The DNA was hybridized with mouse chromosome preparations on electron microscope grids 96. The result is a set of labelled chromosomes 98. The hybridized biotin-labelled probe was then bound to rabbit anti-biotin IgG (an antibody) 100. For electron microscope visualization, colloidal gold was labelled with secondary antibody (goat or sheep directed against rabbit) which binds to the rabbit antibody at sites of hybridized biotin-mouse satellite DNA 102. Alternatively, labelled $Fe_3O_4$ 102 was substituted for colloidal gold. This information also demonstrated that this invention as applied worked as predicted from theory.

In-Situ Hybridization

In-situ hybridization was carried out essentially as described in Narayanswami, et al. (1989) for chromosomes. Coverslips carrying chromosomes were fixed in 0.1% glutaraldehyde in 2×SSC, for 20 min. at room temperature, followed by denaturation for about 10 min. in 2×SSC at about pH 12. In one embodiment, preparations were hybridized overnight at 30° C. in a hybridization buffer containing 50% formamide, 10% dextran sulfate, 1 mM trisodium EDTA, 10 mM Tris at about pH 7.6, 0.2% Ficoll, 1 mg/ml BSA, 40 ug/ml *E. coli* DNA, 0.6M NaCl, and 4 ng/ml denatured biotinylated mouse satellite DNA. Unhybridized probe was removed by rinsing the preparations three times in 2×SCC, for about 20 min. each, at room temperature.

Table 1 (Example 1 described below) presents a sample of the in-situ hybridizations that were carried out by the inventors in 8 separate reactions. The probes were all from the cell line L929, and were biotinylated satellite DNA. The proteins conjugated to the DNA are listed in the right hand column.

Hybrid Detection

Before labelling with biotinylated ferric oxide particles, preparations were incubated successively in rabbit-anti-biotin antibody (purchased from ENZO Biochemicals), biotinylated goat-anti-rabbit antibody (purchased from Jackson Immunoresearch), and 2 ug/ml Streptavidin (BRL). Antibody incubations were carried out in PBS, 0.5M NaCl, 2 mg/ml nuclease free BSA (BRL) for 2 h at 37° C. in a moist atmosphere. Streptavidin incubations were performed in the same buffer, but for about 2 h at room temperature. Preparations were labelled with ferric oxide, colloidal gold, or both. For those preparations labelled with both colloidal gold and ferric oxide, the final incubation in Streptavidin was replaced with an overnight incubation in Streptavidin-20 nm colloidal gold, as described in Narayanswami, et al. (1989). This was followed by labelling with ferric oxide as described below. A few preparations were labelled with 20 nm colloidal gold alone, and this was carried out by reacting hybridized preparations first with rabbit-anti-biotin antibody, for 4 h at 37° C. as above, followed by overnight labelling in 20 nm goat-anti-rabbit-colloidal gold. Biological material was detached from the support as described below.

Labelling with Magnetic Particles

Biotinylated ferric oxide particles were used to label biological material. These particles were ≦0.5 um in average diameter, smaller than commercially available magnetic particles which generally have an average size of 3 um, and smaller than used by Dudin (1988). Bangs Inc. sells small particles in this size range. Their small size permits greater accessibility and, therefore, more efficient labelling than larger particles. For the case of mouse L929 cell chromosomes labelled with mouse centromeric satellite DNA in experiments when the proportion of chromosomes labelled with small particles was compared to those labelled with colloidal gold. The inventors found that magnetic labelling was 80% of that with colloidal gold. It is, thus, feasible to recover a large percentage of the biological material of interest from a preparation by separation in a magnetic field.

In one embodiment, ferric oxide particles were used to provide paramagnetic labelling. 10 mls of a suspension of biotinylated ferric oxide particles were inverted 48 h before use, and the particles allowed to settle out at 4° C. The top 2 mls of the suspension, containing particles of 0.5 um average diameter were removed and diluted twofold (½) in the buffer PBS. Coverslips were each placed in 1 ml of the ferric oxide suspension in single wells of a multi-well tissue culture plate (Falcon 24-well multiwell tissue culture plate inter lid, Becton-Dickinson Cat #3047). A round magnet (Soumaium Cobalt) approximately the same diameter as the coverslip was placed under each preparation, causing the ferric oxide particles to coat the coverslips evenly. The magnet was left in place and the preparations were incubated overnight at room temperature. The next day, the magnet was placed on top of the preparation in order to remove the unbound ferric oxide particles from the coverslips. The coverslips were then removed from the multi-well plate, rinsed three times, for about 20 min. each, at room temperature, in PBS, to remove unbound ferric oxide.

Chromosome Detachment

Figure 12:
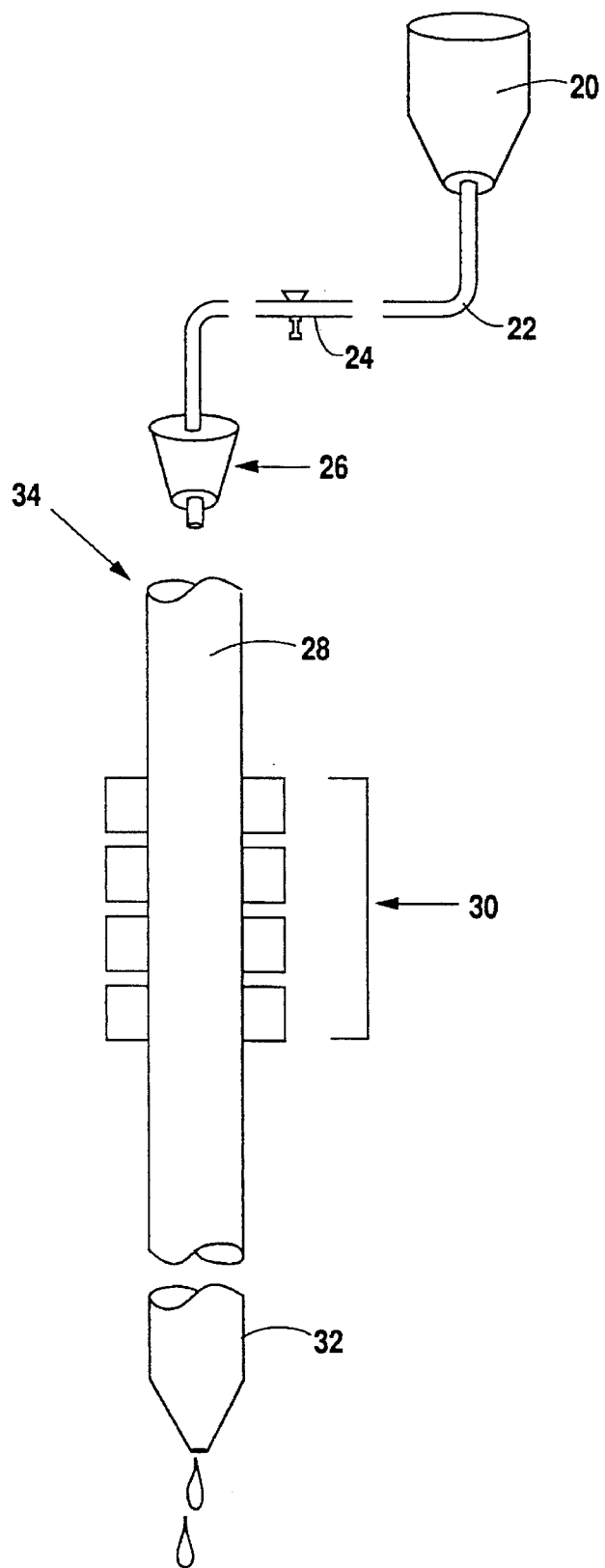
FIG. 12 is a schematic, broken and partially sectioned diagram of a magnetic affinity column used to collect magnetically labelled biological material.
Figure 11:
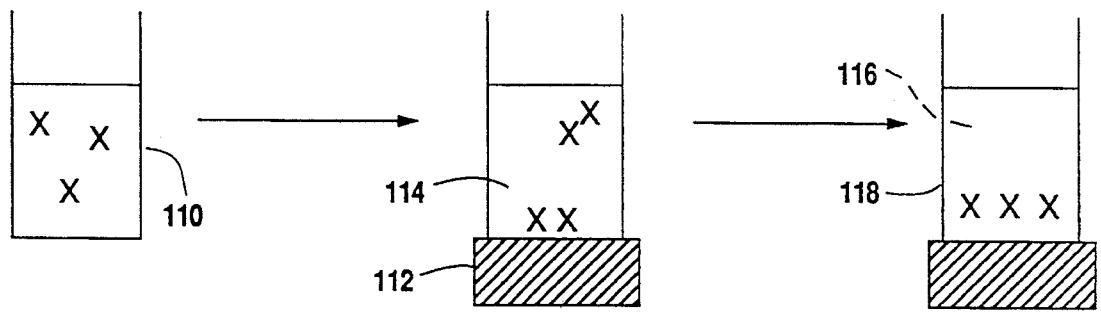
FIG. 11 shows the steps in the procedure to pellet, rinse and purify (sort) the magnetically labelled biological material after it has been released from the support by a releasing agent, for example, DTT.

Ferric oxide labelled preparations were incubated for 2–3 h in 50 mM DTT, 2×SCC, at room temperature. In an illustrative embodiment, chromosomes were dislodged with vigorous pipetting, the supernatant was recovered, and the chromosomes were viewed either using a 40× ocular and phase contrast microscope or in the electron microscope (EM). For electron microscopy, detached chromosomes were centrifuged through a 1M sucrose cushion onto EM grids as described in Narayanswami, et al. (1989) or pelleted with a magnet because of their ferric oxide label (FIGS. 11 and 12). Electron microscopy was performed on a JEOL 100 c electron microscope operated at 80 kV.

FIG. 11 shows the steps in the procedure to pellet, rinse and purify (sort) the magnetically labelled biological material after it has been released from the support by a releasing agent, for example, DTT 110. A magnet 112 is placed beneath a microtiter well 114 to pellet the magnetically labelled biological material. The supernatant 116 is removed. The pellet 118 is subsequently ready to be resuspended.

Sorting in a Magnetic Field

Figure 13:
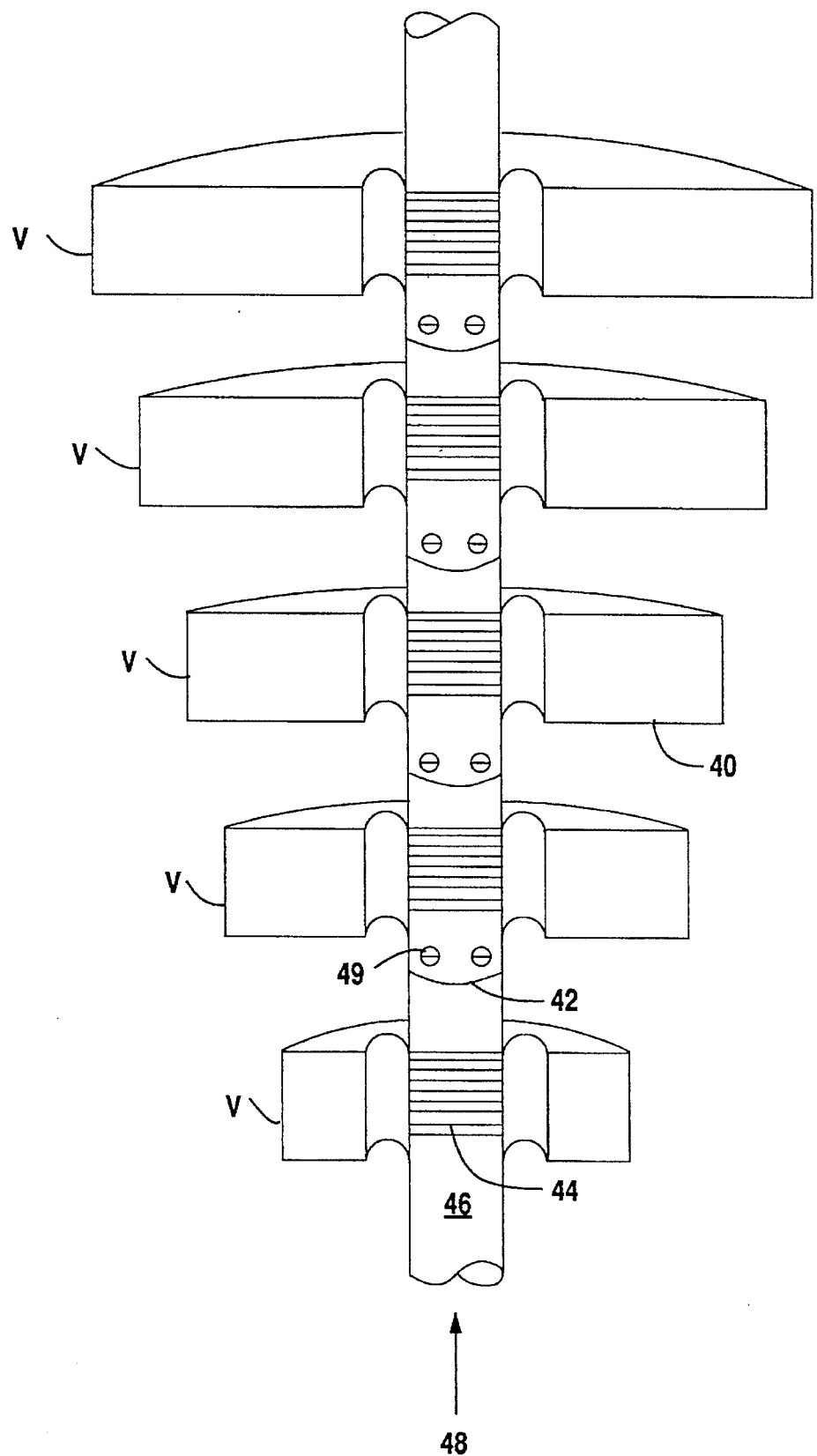
FIG. 13 is a cross-sectional diagram of an embodiment of an apparatus used to collect and separate chromosomes with different amounts of magnetic labels.

FIGS. 12 and 13 illustrate columns which are used to sort magnetized biological material. (FIG. 11 illustrates methods suitable for small amounts.) FIG. 12 illustrates a schematic, broken and partially sectioned diagram of a magnetic affinity column used to collect magnetically labelled biological material. A rinse buffer is passed through a funneling device 20 and a tube 22. The pelleted biological materials 34 are placed on top of the column 28, which is filled with buffer. A clamp 24 and a hypodermic needle 26 control the flow of the buffer which must be slow enough to allow even slightly magnetic particles time to migrate through the column 28 and attach to the inner surface of the column adjacent to the magnets 30. The magnets are in the magnetic ring cupping tube 30. The magnets 30 are attached to the outside of the tube 28. After the non-magnetic particles have passed through the column, the magnets are removed or deactivated and the magnetically labelled fractions are washed out of the tube at 32 and collected.

FIG. 13 is a cross-sectional diagram of an embodiment of an apparatus which may be used to collect and separate chromosomes with different amounts of magnetic labels. There are donut-shaped electromagnets 40 which have copper wire turns proportional to the induced magnetic field at various descending levels of the tube. The direction of flow of the suspension containing the magnetized biological material is upwards 48. The fields are adjustable by means of the adjustable autotransformers (Variac power supply) attached at [v] (not shown). There are joints 42 immobilized by screws 49 above and below each magnetic field. These joints provide access to the collecting screens 44. The collecting screens 44 are on the inside of the collecting tube 46 with some at each magnetic level. At least one screen is contemplated. These are stainless steel, thereby being magnetized. Stainless steel collecting baskets are also within the scope of this invention. A preferred embodiment of the screens is a 2000 μm stainless steel or $FeO_3$ mesh. The collecting tubing 46 is siliconized or otherwise treated to prevent "stickiness." V refers to variac attachments (not shown).

Figure 14:
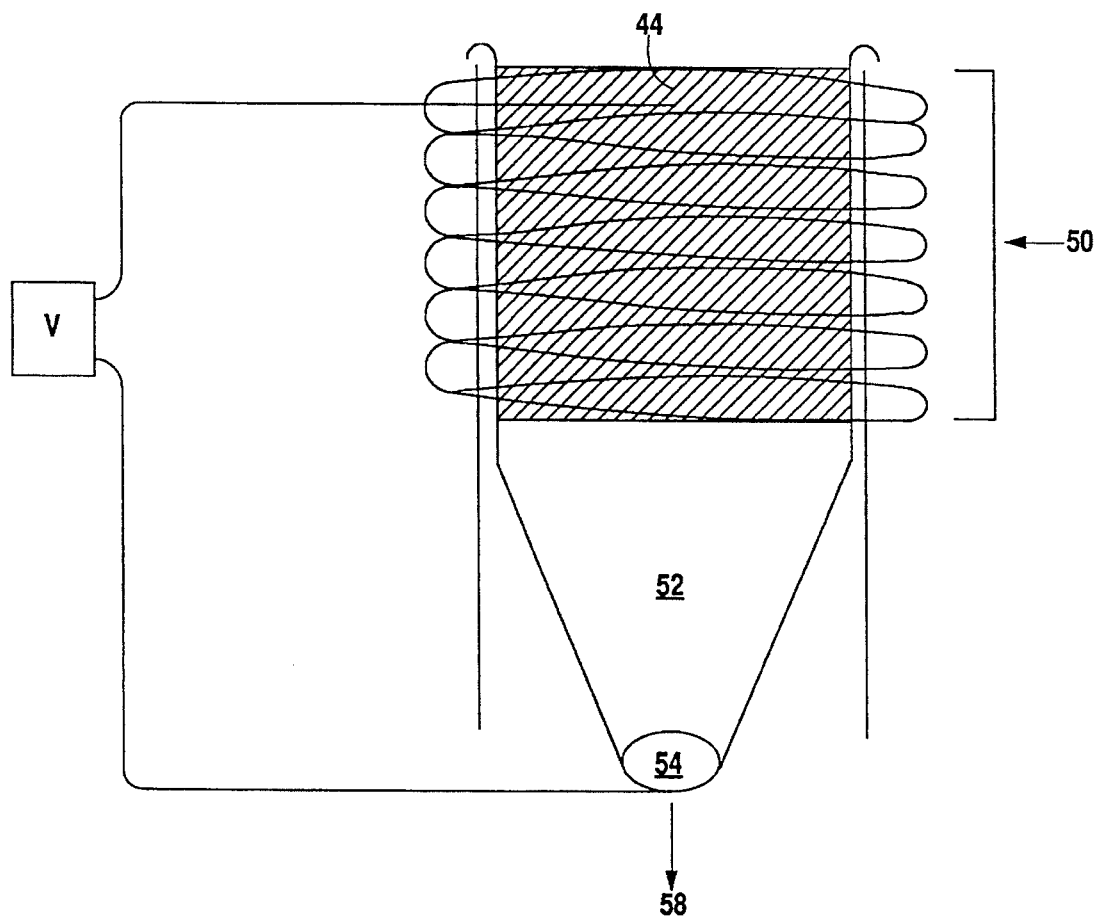
FIG. 14 is a magnafuge, which is a magnet "centrifuge" used to remove the pelleted biological material.

FIG. 14 presents a diagram of a magnafuge, which is a magnet "centrifuge" used to remove the pelleted biological material. An anti-clockwise rotation of copper wire 50 produces a "rail-gun effect" and pellets the chromosomes by a force proportional to the induced magnetic field controlled by a variac-basket (V). The dimensions of the top of the basket are made to hold the collecting screens 44 (FIG. 13). The magnetized biological material are then released to 52 and emerges through the pore 54 after the magnetic force is turned off. Direction of the movement is downwards 58.

EXAMPLES

Example 1

Immobilization and Isolation of Mouse Chromosomes

The mouse L929 cell chromosome system was used to perform experiments designed to assess the efficiency of the immobilization protocol, because large quantities of chromosomes can be easily obtained from this cell line. Mouse satellite DNA was used as a test sequence to determine the effectiveness of labelling protocols because all the mouse centromeres except that of the Y label heavily with this probe (Pardue and Gall, 1970).

Centromeric satellite DNA from mouse chromosomes was used as a probe in a series of reactions to determine binding capacity of various magnetic particles.

Results of a series of reactions in Table 1 illustrate the binding capacity of various magnetic particle compositions.

TABLE 1

In-Situ Hybridization Experiments.

| RE-ACTION # | PROBE | LABEL | PROTEIN CONJUGATION |
|---|---|---|---|
| 1. | L929 sat DNA | biotin | Streptavidin gold (10 nm) |
| 2. | L929 sat DNA | biotin | SA gold (10 nm) - biotin $Fe_3O_4$ |
| 3. | L929 sat DNA | biotin | RαR.biotin - SA gold (15 nm) - biotin $Fe_3O_4$ |
| 4. | L929 sat DNA | biotin | RαR.biotin - SA (naked) - biotin $Fe_3O_4$ |
| 5. | L929 sat DNA | biotin | Rα biotin - GαR gold (15 nm) |
| 6. | L929 sat DNA | biotin | Rα biotin - GαR $Fe_3O_4$ |
| 7. | L929 sat DNA | biotin | Rα biotin - Gα biotin - Rα biotin - Gα R $Fe_3O_4$ |
| 8. | L929 sat DNA | biotin | Rα biotin - GαR.biotin - SA - GαR biotin - Rα $Fe_3O_4$ |

Rα = Rabbit anti-
Gα = Goat anti-

The signal appeared at the centromeres of every chromosome, facilitating detection of low frequency events. Colchicine treated mouse L929 cells were used to prepare chromosome spreads (this is a modification for chromosomes of a method reported by Miller, 1969; see also Hamkalo, et al., 1978).

As a control, reaction 1 (Table 1) was directed to visualize the colloidal gold reaction (see FIG. 7). Reaction 2 bound iron oxide particles to the colloidal gold (see FIG. 8), but at a low frequency. Reaction 4 is a scheme used for signal amplification, addressing the question regarding stearic hindrance, that is, 1) does the signal need to be amplified to be detected by a 500 nm (0.5 micron) $Fe_3O_4$ particle; 2) does signal amplification increase the frequency of signal. The answer to 1 is no. The answer to 2 is yes. A positive amplified reaction product was observed at the centromeric regions (FIG. 9).

Figure 15:
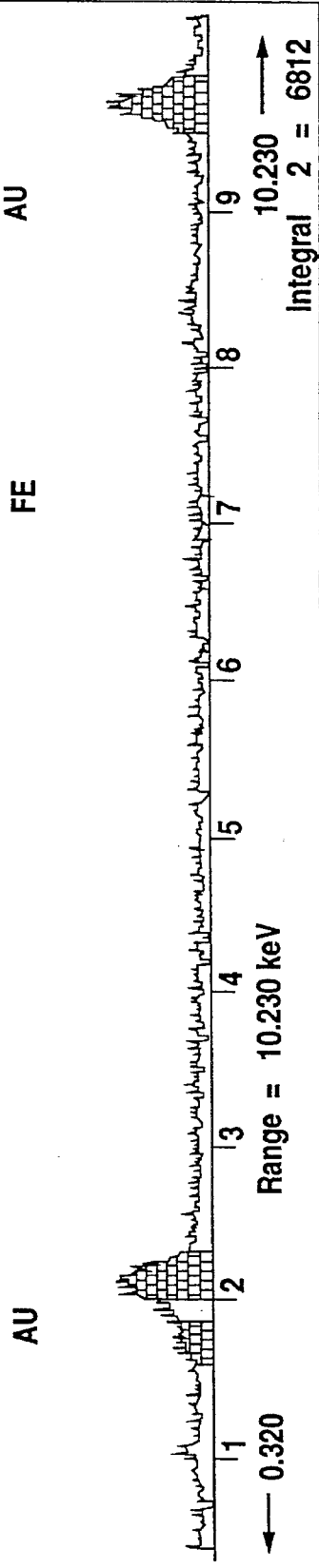
FIG. 15 is a graph which illustrates results of energy dispersive x-ray microanalysis on a non-reactive chromosome from Reaction 3 (Table 1 of Example 1, described hereinafter).
Figure 16:
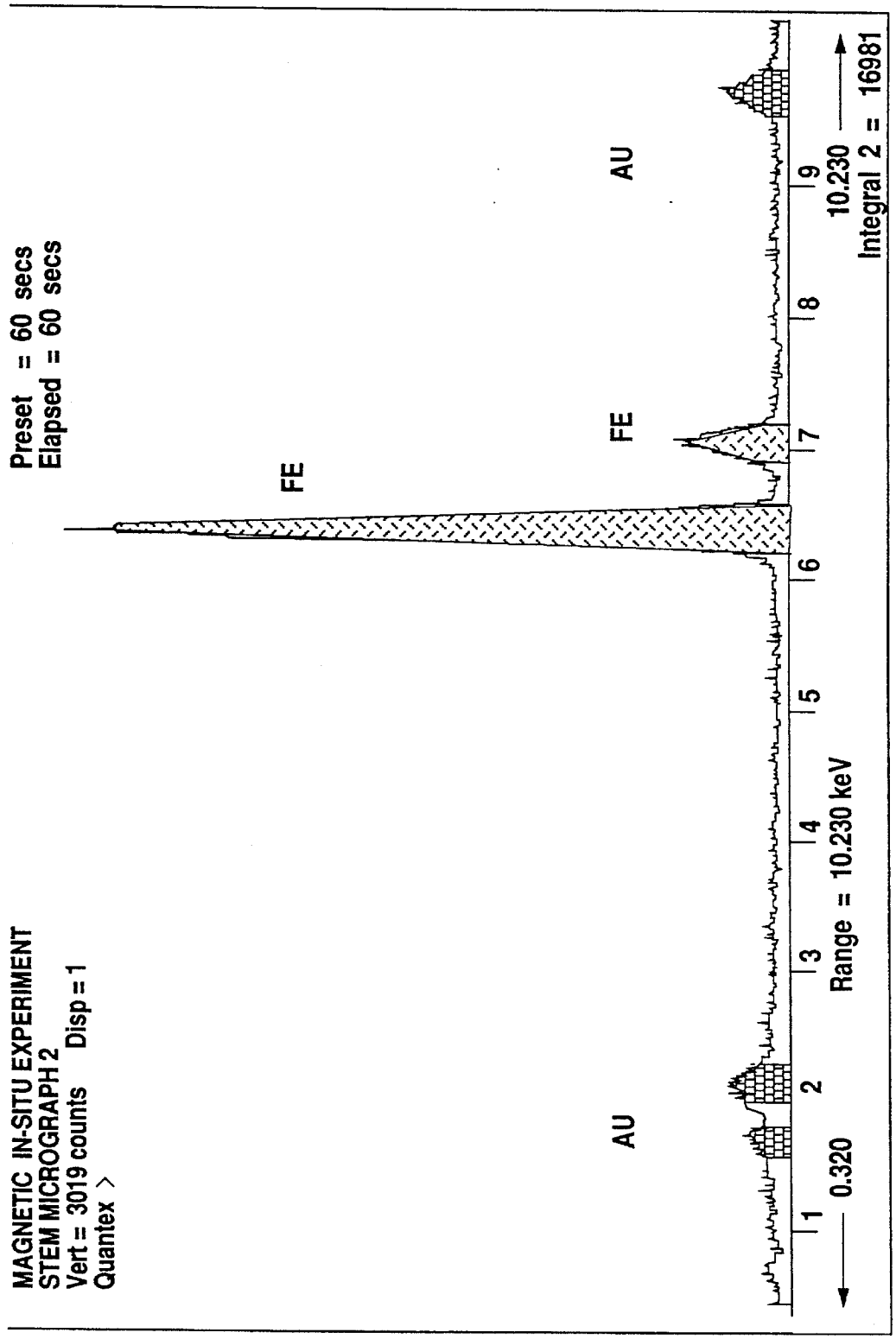
FIG. 16 is a graph which illustrates results of energy dispersive x-ray microanalysis of a reacted chromosome illustrating $K\alpha$ and $K\beta$ peaks for iron (see also FIG. 15).

The reaction product was unequivocally determined to be iron by energy dispersive x-ray microanalysis. FIG. 15 is a graph which illustrates results of energy dispersive x-ray microanalysis on a non-reacted chromosome from reaction 3 (Table 1). In this analysis, electron beams interact with molecules to emit x-rays characteristic of the molecules. L and K refer to electron shells. The Lα and Lβ peaks (to the left) and the Kα and Kβ (to the right, shouldered together) are for gold (Au) and are detected from an EM grid. No iron is present. The Lα and Lβ peaks (to the left) and the Kα and Kβ (to the right and shouldered together), for gold, are detected from the EM grid. There is no iron detectable. FIG. 16 is a graph which illustrates results of energy dispersive x-ray microanalysis of a reacted chromosome illustrating Kα and Kβ peaks for iron (see also FIG. 15). Labelling with magnetic particles was therefor achieved.

Figure 17A:
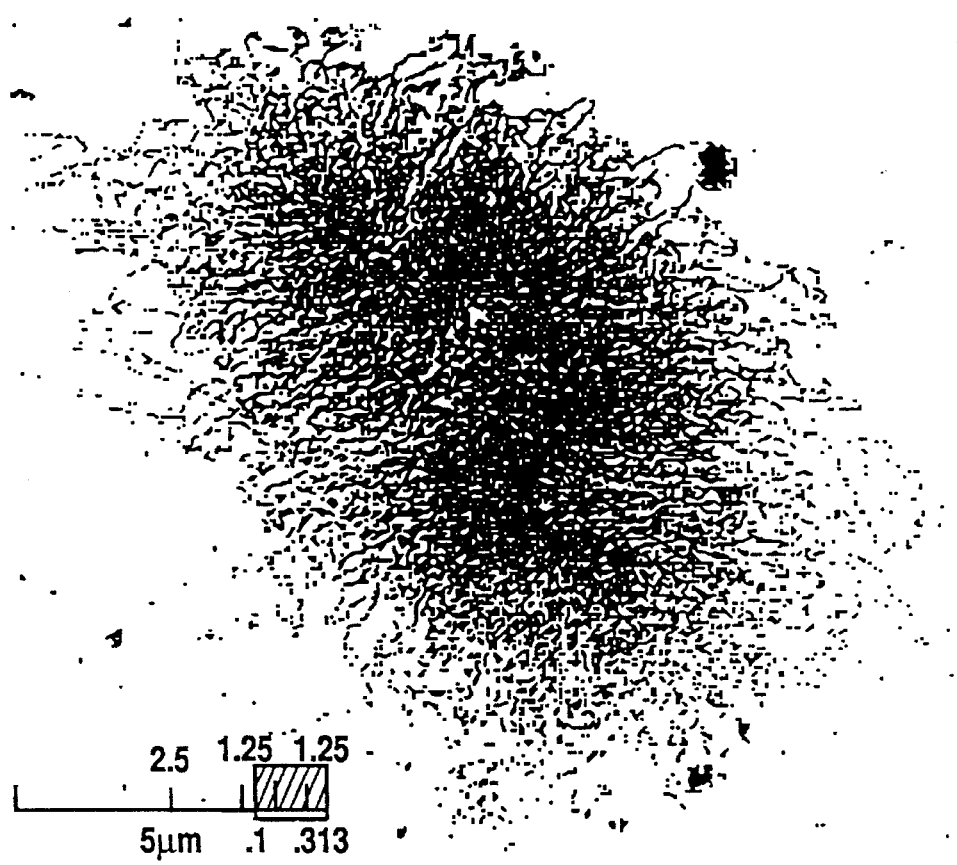
FIGS. 17A and 17B illustrates the size and internal composition of one of the classes of biological materials referred to in this invention, chromosomes: (A) is an electron micrograph of a single chromatid of a mitotic chromosome from an insect (Oncopeltus) treated to reveal loop chromatin fibers that emanate from the central axis of the chromatid; and (B) is a schematic illustration of the many orders of chromosome packing postulated to give rise to the highly condensed metaphase chromosome.
Figure 17B:
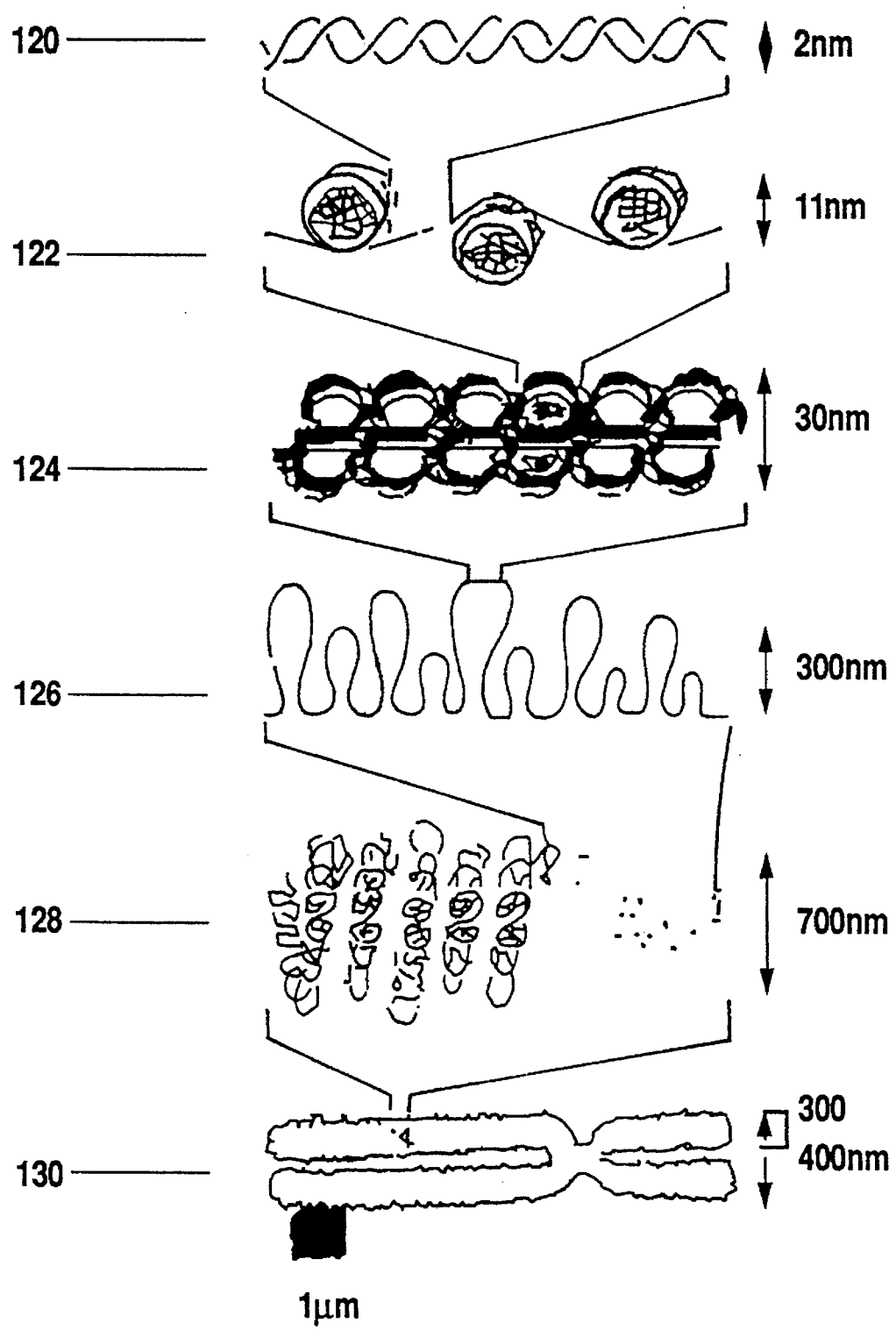

There was no evidence of the steric hindrance that might have been expected based on the supercoiled chromosome structure (FIG. 17). FIG. 17 illustrates the size and internal composition of one of the classes of biological materials referred to in this invention, chromosomes: (A) is an electron micrograph of a single chromatid of a mitotic chromosome from an insect (Oncopeltus) treated to reveal loop chromatin fibers that emanate from the central axis of the chromatid; and (B) is a schematic illustration of the many orders of chromosome packing postulated to give rise to the highly condensed metaphase chromosome. A short region of DNA double helix is illustrated in 120 and packed into "beads on a string" 122. 30 μm chromatin fibers are comprised of packed nucleosomes 124. In an extended form 126, the chromosome may be viewed as a long string, condensed at metaphase 128 to be viewed with the light microscope 130. (adapted from Albert, et al. 1989)

Example 2

Isolation and Sorting of a Human Chromosome from a Mouse-Human Hybrid Cell Line

In order to sort a specific chromosome, and to determine the purity of the sorted preparation, a mouse-human hybrid cell line was used. This line contains a single intact human chromosome No. 1. Cells were mitotically arrested, metaphase cells were harvested by selective detachment and chromosome preparations were immobilized as in Example 1. After immobilization, chromosomes were labelled with a probe for human satellite III (Cooke and Hindley, 1979) which occurs as a large block at a pericentric location on the q-arm of chromosome No. 1. Although satellite III itself occurs on several human chromosomes (Cooke and Hindley, 1979), an alphoid repeat has also been identified that hybridizes specifically to the centromeric region of chromosome No. 1 (Waye, et al., 1987 and Narayanswami, et al., unpublished data) thus allowing sorting and chromosome 1 from both cell hybrids and diploid human tissue. Hybrids were detected with an antibody sandwich procedure followed by reaction with biotinylated ferric oxide in preparation for magnetic isolation. Chromosomes were sorted in a magnetic field as shown in FIG. 11. The sorted preparations were then examined by light microscopy for alteration in morphology and any contamination with mouse chromosomes, which are readily identifiable because of their distinct morphology. Gel electrophoresis was used to estimate the molecular weight of chromosomal DNA. Finally, the DNA from the sorted chromosomes was subjected to blotting and hybridization with appropriate probes (i.e., satellite III) in order to confirm that human chromosome No. 1 had been sorted. This example demonstrates the feasibility of sorting by magnetic particle labelling by isolating chromosome No. 1.

Example 3

Isolation of Chloroplasts by Magnetic Particles

Chloroplast polypeptides are reactive with anti-idiotypic antibodies, providing a label to distinguish chloroplasts by different protein compositions (Pain, et al., 1988). Chloroplasts are magnetically labelled by methods analogous to that used for chromosomes. Initially, chloroplasts are immobilized, fixed and successively incubated with anti-idiotypic antiserum and goat anti-rabbit IgG conjugated to 50 nm magnetic particles. Immobilized chloroplasts are incubated with 50 mM HEPES/KOH, pH 7.7, 0.66M sorbitol for 1 min at 4° C., then with an ice-cold aldehyde fixative (0.05% glutaraldehyde+25% paraformaldehyde) in the same buffer for 30 min at 4° C. After washing with buffer A (50 mM HEPES/KOH, pH 7.7, 0.33M sorbitol, 40 mM $KOA_c$, 2 mM Mg $(OAc)_2$) containing 10 mM $NH_4Cl$ and buffer A plus 2% BSA (bovine serum albumin), the samples are incubated with decomplemented anti-idiotypic rabbit antiserum (1:500) in buffer B (Buffer A, 1% BSA, 1 mM phenyl methyl sulphonyl fluoride (PNSF)) for 2 h at room temperature, washed and incubated with goat IgG (100 $\mu l^{-1}$) in buffer B. The samples are washed as above and incubated with goat anti-rabbit IgG conjugated to colloidal gold if desired (10 nm, 1:50, Janssen). The samples are washed with Buffer A, immersed in Karnovsky's aldehyde fixative containing 0.33M sorbitol (1 h), osmicated (1 h), stained with uranyl acetate (2 h) and dehydrated in graded series of ethanol as described (Kanwor, Y. S. and Farguhar, M. G., *J. Cell. Biol.*, 81:137–153 (1979)).

Protoplasts are lysed by physical disruption into the isolation buffer described in Gruissem, et al. (1983) or Schreiber, et al. (1988). Chloroplast isolation is performed according to conditions established by Grossman, et al. (*J. Biol. Chem.* 257:1558–1563, 1982) and magnetic immunoprecipitation as described in the present application. Sorting is accomplished in a magnetic field.

Example 4

Isolation of Mitochondria or the Golgi Apparatus

The procedures of Example 3 are generally followed, but antibodies to the outer membrane proteins or to a transmembrane protein in Golgi, are used for labelling.

METHODS

The following are more detailed protocols of specific embodiments of this invention.

A. Preparation of coverslips

1. Glass coverslips preferably round, and which are about 1 cm in diameter, were acid washed, usually in HCl. Coverslips were then rinsed thoroughly in distilled water and dried.

2. The coverslips were silanated according to methods of Pierce Chemical Co. (see section H1).

3. Silanated coverslips were air dried and stored at room temperature until needed.

4. The coverslips were prefixed by incubating each coverslip in 1 mM dithiobis-sulfa succinimidyl propionate (DTSSP) (freshly made up in 2×SSC) for 1 h at room temperature in a petri dish. The DTSSP solution generally was placed only on the top surface of the coverslip with a Pasteur pipette. Other reversible crosslinkers, e.g., SPDP, may be substituted. Mitotic cells were harvested from the tissue culture vessels while the coverslips were prefixing.

B. Chromosome Preparation 1. 2 T75 tissue culture flasks of cells were initiated by standard procedures, e.g., line L929. This is enough to prepare about 8 coverslips. If more cells are needed, 4 T75 flasks may be set up. When growth of cells in the flasks was approximately 50% confluent (100% confluent would be at the point where cell growth covers the entire bottom surface area of the culture vessel), Colcemid was added to arrest the cell division (50–80 ng/ml, Gibco) and incubated at 37° C. overnight, or up to 24 h.

2. The metaphase[2] cells were collected by shaking them off the bottom of the flasks. Three hard bumps was usually sufficient to dislodge all the metaphase cells.

[2]"Metaphase" refers to all phases of the cell cycle wherein chromosomes are sufficiently distinct (condensed) to be isolatable. This usually refers to prometaphase through later metaphase.

3. The metaphase cells were pelleted by centrifugation (2000 rpm for about 10 min.) and resuspended at 25° C. in about 1 ml of the same culture medium. This amount was determined empirically and need not be exact.

4. After the coverslips had prefixed for 1 h, (see step A4) the microcentrifugation chambers were set up. The transparent cap of a 15 ml Falcon tube was filled with 1M sucrose at a pH of about 8.5 to a depth of about 1 cm. The coverslip was dipped in the sucrose with the prefixed side up and should rest on the raised central portion of the chamber. There should be few mm of sucrose above the coverslip. This amount may be determined empirically and need not be exact.

5. Cells were lysed in about 1% Nonidet P-40 (a detergent) at about pH 8.5. Using a Pasteur pipette, about 5 drops of cells were placed in a glass test tube. Five drops of the detergent, Nonidet P-40, were added, mixed gently with the cells, and incubated at room temperature for 1 min. The lysate was layered over the sucrose cushion in the chamber, and centrifuged for 5 min. at 3200 rpm (2500 g) at room temperature in 50 ml swinging buckets in a Sorvall GLC-28 centrifuge, or the equivalent.

6. The coverslip was removed from the chamber using watchmakers' forceps, and rinsed well in 0.4% Kodak Photoflo 200, at about pH 8.5, to remove the sucrose. The coverslips were rinsed briefly, about 5 min., in an excess of 2×SSC, 150 mM glycine in a beaker (50–100 mls buffer) to quench the DTSSP. The chromosomes on the coverslips were examined at this point using a 40× phase contrast microscope. To do this, sufficient 2×SSC to cover the glass (a few drops) was placed on the coverslip which was on a slide. The coverslip was kept wet at all times from this point on.

C. In-Situ Hybridization

1. The hybridization buffer was prepared according to Narayanswami, et al. (1989). The desired probe (e.g., biotinylated mouse satellite DNA) was added to 4 μg/ml and the mixture was heated for about 5 min. at 100° C., e.g., in a boiling water bath to denature the probe. The mixture was fast cooled on ice for about 2 min. and centrifuged briefly in a microcentrifuge to bring down any condensed buffer on the sides of the tube. The centrifuged buffer was kept on ice until needed. 50 ul buffer per coverslip was prepared.

2. The coverslips were fixed in freshly prepared 0.1% glutaraldehyde (EM grade, Polysciences) in 2×SSC for 20 min. at room temperature. The coverslip was covered with a few drops of 0–1% glutaraldehyde, 2×SSC, and then placed in a Petri dish.

3. The coverslips were rinsed briefly in 2×SSC.

4. Coverslips were denatured for 10 min. in 2×SSC at pH12 (about 12 drops of 10M NaOH in 50 ml of 2×SSC), rinsed in Photoflo, and placed on a clean glass slide.

5. 50 ul of the hybridization buffer containing the denatured probe was quickly pipetted onto each coverslip. The coverslips were transferred to a wet box (a box containing moist paper towels, and having a lid) and hybridized at 30° C. overnight (12–15 h).

6. The coverslips were placed in a rack in a beaker. The coverslips were rinsed three times, for about 20 min. each at room temperature in 2×SSC (using about a 100 ml volume) to remove unhybridized probe.

D. Hybrid Detection

1. All of the following antibody incubations were performed in a physiological buffer, e.g., PBS, 0.5M NaCl, 2 mg/ml BSA (bovine serum albumin) from BRL for 2 h, at 37° C., in Petri dishes, in a wet box, unless otherwise stated. Incubations with Streptavidin were performed at room temperature, but otherwise as stated above.

2. For labelling with biotinylated ferric oxide particles, the coverslips were incubated successively in 1/500 rabbit-anti-biotin, followed by 1/500 biotinylated goat-anti-rabbit antibody, and then in 2 ug/ml Streptavidin (Bethesda Research Laboratories). After each incubation, in order to remove any unbound antibody, the coverslips were rinsed 3 times, for about 10 min. each, at room temperature, in PBS, 0.5M NaCl, in racks in a beaker (each rinse using about 100 mls vol).

3. For labelling with colloidal gold alone, preparations were first incubated in 1/500 rabbit-anti-biotin for 4 h at 37° C., and rinsed as described in D2. This procedure was followed by overnight incubation in 1/7 goat-anti-rabbit-20 mm colloidal gold. Coverslips were rinsed 3 times for about 20 min. each in 1% BSA buffer (1% BSA, Fraction V, Sigma, 0.9% NaCl, 0.02M sodium azide, 20 mM Tris at pH 8.2) and chromosomes were detached as described in Section F.

4. If preparations were to be labelled with both colloidal gold and ferric oxide, overnight labelling in Streptavidin 20 nm gold was substituted for the Streptavidin incubation. Coverslips were then washed in 1% BSA as above, followed by labelling in ferric oxide as described in Section E. Chromosomes were detached as described in Section F.

E. Labelling with Ferric Oxide Particles

1. Biotinylated ferric oxide particles of a mean diameter of about 50 nm to 2 microns prepared by inverting about 10 mls of buffered suspension 48 h before it was needed and allowing the preparation to settle out at 4° C. The top 2 ml of the suspension were used for labelling. This layer was removed with a Pipetman.

2. The ferric oxide was diluted two fold in PBS just before use.

3. Each coverslip was placed in 1 ml of the ferric oxide suspension in the well of a cell culture plate (Falcon) or a 24-well multiwell tissue culture plate with a lid (#3047 Becton-Dickinson). The plate was covered with its lid.

4. A small round magnet was placed underneath the well such that the ferric oxide particles covered the coverslip evenly. The rationale here was to force the magnetic beads to bind the streptavidin on the chromosome by using the magnet to keep these 2 components in forced contact. The magnet was left in place, and the coverslip was kept at room temperature overnight.

5. The magnet was removed from underneath the well and placed on the lid of the plate, over the well containing the coverslip. The unbound ferric oxide will come off the preparation, and when the plate has been opened, can be removed the supernatant over the coverslip with a pipette and discarded. The ferric oxide was replaced in the well with 1–2 ml PBS, the coverslip was removed, and rinsed in racks in a beaker (as described above) 3 times, for about 20 min. each, in PBS, at room temperature.

F. Detachment of Chromosomes from Support

1. The coverslips were incubated for 2.5 h in 50 mM dithiothreitol (DTT) in 2×SCC, at room temperature, in a Petri dish. Preferably, a few drops of DTT were placed on the coverslip.

2. Pipetting vigorously with a Pasteur pipette was used to dislodge the chromosomes from the support. The supernatant containing the related chromosomes was removed. Detachment can be monitored under a 40× ocular using phase contrast microscopy. For electron microscope (EM) observation, the chromosomes may be centrifuged through 1M sucrose, onto grids, as described in Rattner and Hamkalo (1978).

G. Mechanism of SPDP Reaction Using Chromosomes as the Biological Material

1. Primary amines on controlled pore glass LCAA are converted to active sulfhydryls.

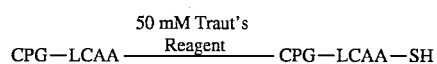

2. Primary fixation achieves coupling of the reversible cross linker (SPDP) to the CPG-LCAA-SH.

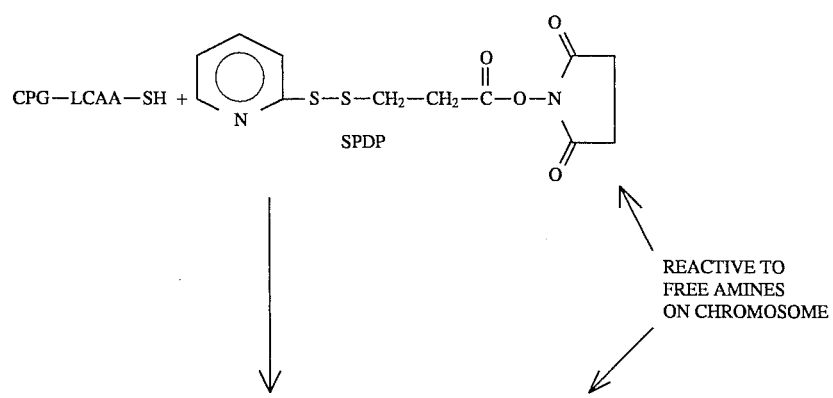

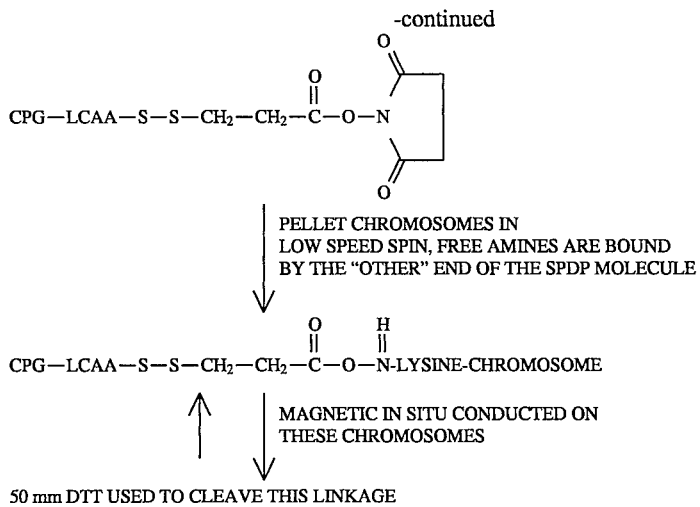

50 mm DTT USED TO CLEAVE THIS LINKAGE

The SPDP reaction binds the chromosome with a limited number of cross linkers, which can be easily cleaved by low concentrations of DTT, hence chromosome recovery is higher, and chromosome integrity is retained.

H. DTTSP Reaction Using Chromosomes as the Biological Material

1. Silanation of cover glasses
   a. Rinse with 1M HCl
   b. Rinse with distilled $H_2O$—about three times
   c. Rinse with dry acetone—about three times
   d. Reflux about 2 hrs—overnight with Pierce #80379 N-(2-Aminoethyl)-3-aminopropyltrimethoxysilane; this is prepared to 25% (v/v) in dry acetone
   e. Rinse with dry acetone—about three times
   f. For quality assurance detect presence of free amines may be detected with 1% fluoraldehyde [this is O-Phthaladehyde—Pierce Chemical Co. #26015] in distilled water and read in a fluorometer.

2. Free amines are provided to glass (and $Fe_3O_4$ particles) as diagrammatically represented below:

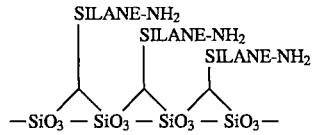

3. The derivatized glass providing free amines is reacted with DTSSP as follows:

While the invention is susceptible to various modifications and alternative forms, specific embodiments thereof have been shown by way of example in the drawings and herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for, or teach methodology, techniques, and/or compositions employed herein.

Reference 1. Albert, B., Bray, D., Lewis, J., Raff, M., Roberts, K., Watson, J. D. (1989) Chap. 9, The Cell Nucleus, Mol. Cell. Biol., Garland Publishing Inc. (N.Y.).

Reference 2. Anderson, L. and Mosbach, K. (1977) Magnetic Ferrofluids for Preparation of Magnetic Polymers and Their Application in Affinity Chromatography. Nature, 270:259.

Reference 3. Bebee, R. and Gebeyehu, G. (1990) DNA Capture Reagent: A Novel Reagent for the Rapid Isolation of DNA from Complex Biological Fluids and Buffer Solutions. Focus 12, no. 3:77–78.

Reference 4. Berman, J. S., and Center, D. M. (1987) Chemotactic Activity of Porcine Insulin for Human T Lymphocytes in Vitro. Journal of Immunology, 138:2100.

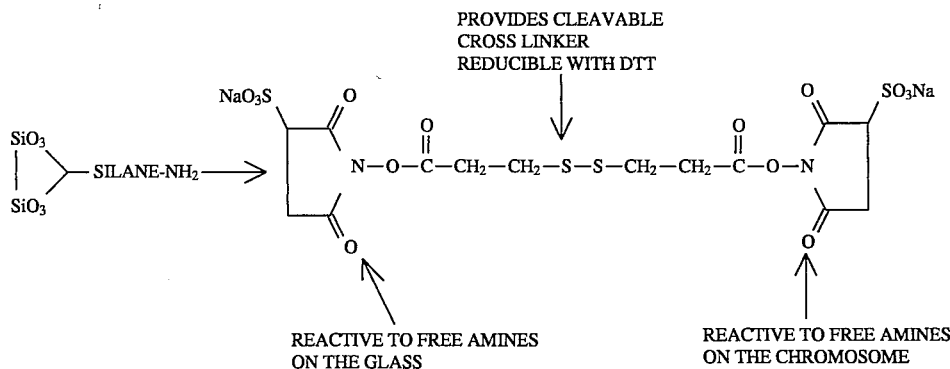

Reference 5. Cashmore, A., Szabo, L., Tinko, M., et al. (1985) Import of Polypeptides into Chloroplasts; a Review. Bio/Technology, 3:803–807.

Reference 6. Cooke, H. J. and Hindley, J. (1979) Cloning of Human Satellite III DNA: Different Components Are on Different Chromosomes. Nuc. Acids Res. 10:3177–3197.

Reference 7. Cooke, A., Tolmie, J. L., et al. (1989) Detection of an Unbalanced Translocation (4;14) in a Mildly-Retarded Father and Son by Flow Cytometry. Hum. Genet. 83:83–87.

Reference 8. Cruikshank, W. W., Berman, J. S., Theodore, A. C., Bernardo, J. and Center, D. M. (1987) Lymphokine Activation of T4 & T Lymphocytes and Monocytes. Journal of Immunology, 138:3818.

Reference 9. Czerlinski, G., Senyei, A., and Widder, K. (1978) Magnetic Guidance of Drug Carrying Microspheres. Journal of Applied Physics, 49:3578.

Reference 10. Damha, M. J., Giannaris, P. A., et al. (1990) An Improved Procedure for Derivatization of Controlled-Pore Glass Beads for Solid Phase Oligonucleotide Synthesis. Nucleic Acids Res. 18:3813–3821.

Reference 11. Darzynkievicz, Z. and Crissman, H. O. (1990) Flow Cytometry, Academic Press, San Diego, Calif.

Reference 12. Dudin, G., Cremer, T., et al. (1987) A Method for Nucleic Acid Hybridization to Isolated Chromosomes in Suspension. Hum. Genet. 76:290–292.

Reference 13. Dudin, G., Steegmayer, E. W., et al. (1988) Sorting of Chromosomes by Magnetic Separation. Human Genet. 80:111–116.

Reference 14. Gelvin, S. B. and Schilperoort, R. A. (eds) (1988) Plant Molecular Biology Manual, Kluwer Academic Publishers, Boston.

Reference 15. Giaever, I. (1976) Magnetic Separation of Biological Particles. U.S. Pat. No. 3,970,518.

Reference 16. Gray, J. W. (1990) Flow Cytogenetics, Academic Press, San Diego, Calif.

Reference 17. Gruissem, W., Greenberg, B. M., Zurawski, G., et al. (1983) Biosynthesis of Chloroplast Transfer RAA in a Spinach Chloroplast Transcription System. Cell, 35:815–828.

Reference 18. Harris, P., Morton, C. C., Guglielmi, P., et al. (1986) Mapping by Chromosome Sorting of Several Gene Probes Including C-myc, to the Derivative Chromosomes of a 3;8 Translocation Associated with Familial Renal Cancer. Cytometry 7:589–594.

Reference 19. Howell, K., Gruenberg, J., et al. (1988) Immuno-Isolation of Subcellular Components. In: Morre D. J., et al. (eds.) Cell-Free Analysis of Membrane Traffic. Liss, N.Y. pp. 77–90.

Reference 20. Hutchison, N. J., Langer-Safer, P. R., et al. (1982) In-Situ Hybridization at the Electron Microscope Level: Hybrid Detection by Autoradiography and Colloidal Gold. The Journal of Cell Biology 95:609–618.

Reference 21. Hunter, J. A. (1982) Ferrography—A New Method for Isolation of Particles from Biological Fluids. Journal of Clinical Pathology, 35:689.

Reference 22. June, C., Ledbetter, J. A., Gillespie, M. M., Lindsten, Tullia and Thompson, C. B. (1987) T-Cell Proliferation Involving the CD28 Pathway is Associated with Cyclosporine-Resistant Interleukin-2 Gene Expression. Molecular and Cell Biology, 7:4473.

Reference 23. Kvalheim, G., Fodstad, O., Pihl, A., et al. (1987) Elimination of B-lymphoma Cells from Human Bone Marrow: Model Experiments Using Monodisperse Magnetic Particles Coated with Primary Monoclonal Antibodies. Cancer Res. 47:846–851.

Reference 24. Lea, T., Vartdol, F., et al. (1985) Magnetic Monosized Polymer Particles for Fast and Specific Fractionation of Human Mononuclear Cells. Scand. J. Immunol. 22:207–216.

Reference 25. Lehman, J. (1990) Brave New Biosensors. Biotechnology 8:729–731.

Reference 26. Linette, G. P., Hartzman, R. J., Ledbetter, J. A., June, C. H. (1988) HIV-1-Infected Cells Show a Selective Signaling Defect after Perturbation of CD3/Antigen Receptor. Science, 241:573.

Reference 27. Manning, J., Hershey, N. D., et al. (1975) A New Method for In-Situ Hybridization. Chromosome (Berl.) 55:107–117.

Reference 28. Margel, S., Beitler, U. and Ofarim, M. (1982) Polyacrolein Microspheres as a New Tool in Cell Biology. J. Cell Sci. 56:157.

Reference 29. Margel, S., Rembaum, A., and Zisblatt, S. (1979) Polyglutaraldehyde: A New Reagent for Coupling Proteins to Microspheres and for Labeling Cell Surface Receptors. II. Simplified Labeling Method by Means of Non-Magnetic and Magnetic Polyglutaraldehyde Microspheres. Journal of Immunological Methods, 28:341.

Reference 30. Menz, E. T., Havelick, J., et al. (1986) Magnetic Affinity Chromatography: An Emerging Technique. American Biotechnology Laboratory, September/October.

Reference 31. Merrifield, et al. (1963) JACS, 85:2149.

Reference 32. Molday, R. S., Rembaum, A., and Yen, S. P. S. (1977) Application of Magnetic Microspheres in Labeling and Separation of Cells. Nature, 268:437.

Reference 33. Morimoto, Y. (1983) Magnetic Guidance of Ferro-Colloid Entrapped Emulsion for Site Specific Drug Delivery. The Chemical and Pharmaceutical Bulletin, (Tokyo), 1:279.

Reference 34. Morimoto, Y. (1981) Biomedical Applications of Magnetic Fluids II. Journal of Pharmacobiodynamics, 4:624.

Reference 35. Mosbach, K., and Schroder, U. (1979) Preparation and Application of Magnetic Polymers for Targeting of Drugs, FEBS Letters, 112.

Reference 36. Moyzis, R. K., Albright, K. L., et al. (1987) Human Chromosome-Specific Repetitive Sequences: Novel Markers for Genetic Analysis. Chromosome (Berl) 95:375–386.

Reference 37. Narayanswami, S., Lundgren, K., and Hamkalo, B. A. (1989) Deoxyribonucleic Acid Sequence Mapping on Metaphase Chromosomes by Immunoelectron Microscopy. Scanning Microscopy Supplement 3:65–76.

Reference 38. Narayanswami, S. and Hamkalo, B. A. (1990) High Resolution Mapping of Xenopus laevis 5S and Ribosomal RNA Genes by EM In-Situ Hybridization. Cytometry 11:144–152.

Reference 39. Narayanswami, S., Kausch, A. P., and Hamkalo, B. A. (1990) Reversible Immobilization of In-Situ Hybridized Chromosomes. A New Approach to Chromosome Sorting. Submitted.

Reference 40. Narayanswami, S., Lucci, J. A. III, et al. (1990) Interleukin-2 Stimulated Mouse Spleen Cultures: A Method for Generating Large Numbers of Diploid Cells and Metaphase Chromosomes. In preparation.

Reference 41. Newbower, R. (1973) Magnetic Fluids in the Blood, IEEE Transactions on Magnetics, MAG.-9, 447.

Reference 42. Padmanabhan, R., Corsico, C. D., Howard, T. H., et al. (1988) Purification of Transiently Transfected Cells by Magnetic Affinity Cell Sorting. Anal. Biochem., 170:341–348.

Reference 43. Pardue, M. L., and Gall, J. G. (1970) Chromosomal Localization of Mouse Satellite DNA. Science 168:1356–1358.

Reference 44. Ranney, D. F., Senyei, A. E. and Widder, K. (1979) Magnetically Responsive Microspheres and Other Carriers for the Biophysical Targeting of Antitumor Agnets. Advances in Pharmacological Chemotherapy, 16:213.

Reference 45. Rattner, J. B. and Hamkalo, B. O. (1978) Higher Order Structure in Metaphase Chromosomes. The 250 Å Fiber. Chromosome (Berl.) 69:363–372.

Reference 46. Rembaum, A. and Dreyer, W. J. (1980) Immunomicrospheres: Reagents for Cell Labeling and Separation. Science, 208:364.

Reference 47. Scarpelli, D., Senyei, A. and Widder, K. (1978) Magnetic Microspheres: A Model System for Site Specific Drug Delivery in Vivo. Proceedings of the Society for Experimental Biology and Medicine, 58:141.

Reference 48. Schreiber, P. H., Reiss, B. and Kuntz, M. (1988) Subcellular Targeting of Proteins In Vivo and In Vitro. In Gelvin and Schilperoort, pp. 1–22.

Reference 49. Schroeder, U., Segren, S., Gemmefors, C., et al. (1986) Magnetic Carbohydrate Nonparticles for Affinity Cell Separation. J. of Immunol. Methods 93:45–53.

Reference 50. Senyei, A. E. and Widder, K. (1981) Drug Targeting: Magnetically Responsive Albumin Microspheres—A Review of the System to Date. Gynecology and Oncology, 12:1.

Reference 51. Senyei, A. E. and Widder, K. (1981) Magnetic Microspheres. J. of Histochemical Cytochemistry.

Reference 52. Spangrude, G. J., Heimfeld, S. and Weissman, I. L. (1988) Purification and Characterization of Mouse Hematopoietic Stem Cells. Science, 241:58–62.

Reference 53. Staros, J. V. (1982) N-hydroxysulfoccinimide Active Esters: Bis-(N-hydroxysulfosuccinimide) Esters of Two Dicarboxylic Acids are Hydrophilic, Membrane Impermeant Protein Crosslinkers. Biochemistry 21:3950–3955.

Reference 54. Sugibayashi, K. (1982) Biomedical Applications of Magnetic Fluids. Biomaterials.

Reference 55. Uhlen, M. (1989) Magnetic Separation of DNA. Nature 340:733–734.

Reference 56. Viegas-Pequignot, E., Dutrillaux, B. et al. (1989) Mapping of Single-Copy DNA Sequences on Human Chromosomes by In-Situ Hybridization with Biotinylated Probes: Enhancement of Detection Sensitivity by Intensified-Fluorescence Digital-Imaging Microscopy. Proc. Natl. Acad. Sci. USA 86:582–586.

Reference 57. Waye, J. S., Durfy, S. J., Pinkel, D., et al. (1987) Chromosome-Specific Alpha Satellite DNA from Human Chromosome 1: Hierarchical Structure and Genomic Organization of a Polymorphic Domain Spanning Several Hundred Kilobase Pairs of Centromeric DNA. Genomics 1:43–51.

Reference 58. Wilchek, M. and Boyer (eds) E. A. (1990) Avidin-Biotin Technology, v. 184, Academic Press, San Diego, Calif.

Reference 59. Wu, D. and Walters, R. R. (1988) Protein Immobilization of Silica Supports: A Ligand Density Study. J. Chromat. 458:169–174.

What is claimed is:

1. A method for the magnetic labelling of a chromosome or chloroplast cellular component comprising the following steps:
   (a) binding said cellular component to a binding composition comprised of an antibody or nucleic acid in the case of chromosome isolation, or antibody in the case of chloroplast isolation; and
   (b) labelling said binding composition with magnetic particles having an average diameter less than about 2 µm.

2. A method for the isolation of a chromosome or chloroplast cellular component comprising the following steps:
   (a) reversibly anchoring said cellular component to a support with a DTSSP or SPDP linker;
   (b) binding said cellular component to a binding composition comprised of an antibody in the case of chromosome or chloroplast isolation, or nucleic acid in the case of chromosome isolation;
   (c) labelling said binding composition with magnetic particles having an average diameter less than about 2 µm;
   (d) releasing said cellular component from the support to form free, magnetized cellular components; and
   (e) isolating said cellular component by applying a magnetic force to said free, magnetized cellular components.

3. The method of claim 2, wherein the cellular component is a chromosome.

4. The method of claim 2, wherein the cellular component is a chloroplast.

5. The method of claim 2, wherein the binding composition which binds to the cellular component comprises nucleic acid probes.

6. The method of claim 2, wherein the cellular component comprises polypeptides and the binding composition comprises antibodies to the polypeptides.

7. The method of claim 2, wherein the magnetic particles comprise ferric oxide particles.

8. The method of claim 2, wherein the support comprises a silane treated surface that anchors the cellular component to the support, and a cleavable cross-linking agent which crosslinks between the cellular component and the support.

9. The method of claim 8 wherein the surface is treated with the silane N-(2-aminoethyl)-3-aminopropyl trimethoxysilane.

10. The method of claim 8 wherein the cleavable cross-linking agent comprises SPDP or DTSSP.

11. The method of claim 2, wherein the support comprises a glass coverslip.

12. The method of claim 2, wherein the support comprises controlled pore glass beads (CPG).

13. The method of claim 12, wherein the controlled pore glass beads are attached to long chain alkylamine linker arms.

14. The method of claim 2, wherein the support comprises polymer beads.

15. The method of claim 14, wherein the polymer beads are treated with oligopeptides, said oligopeptides each terminating in a cleavable amino group.

16. The method of claim 2, wherein the binding composition comprises a label.

17. The method of claim 16, wherein the label comprises a biotinylated fluorescent marker.

18. The method of claim 5, wherein the probes are capable of hybridizing to unique repetitive sequences of the centromeric regions of specific chromosomes.

19. The method of claim 1 wherein the particles are from about 50 nm to about 0.5 microns in diameter.

20. The method of claim 2, wherein the magnetic particles comprise colloidal gold.

21. A method of separating a chromosome or chloroplast cellular component comprising the following steps:
   (a) binding a supported, cellular component to a binding composition comprised of an antibody in the case of chromosome or chloroplast isolation, or nucleic acid in the case of chromosome isolation;

(b) labelling said bound cellular component with a magnetic particle having an average diameter of less than about 2 μm; and (c) magnetically separating the resulting labelled cellular component.

22. The method of claim 21 wherein the cellular component comprises a chromosome and the binding composition comprises a nucleic acid probe.

23. The method of claim 21 wherein the cellular component comprises a protein and the binding composition comprises an antibody directed to that protein.

24. The method of claim 21 wherein said cellular component is supported by means mounting said cellular component on a silane treated support by a disulfide-containing bifunctional reversible crosslinker.

25. The method of claim 21 wherein the particle is from about 50 nm to about 0.5 microns in diameter.

26. A method of sorting chromosomes to achieve purified suspensions thereof, said method comprising the following:

(a) anchoring the chromosomes to a support by means of a disulfide-containing bifunctional reversible linker;

(b) hybridizing the supported chromosomes with a binding nucleic acid or antibody binding composition to form a complex;

(c) labelling the complex with magnetic particles having an average diameter less than about 2 μm;

(d) releasing the complex from the support; and (e) sorting the released chromosomes by means of a magnetic force.

27. The method of claim 26, wherein the binding composition comprises nucleic acid sequence probes.

28. The method of claim 26, wherein the binding composition comprises antibodies.

29. A method of sorting chromosomes to achieve purified preparations thereof, said method comprising the following steps:

(a) anchoring the chromosomes to a support by means of a reversible DTSSP or SPDP linker;

(b) hybridizing the supported chromosomes with a binding composition comprised of an antibody or nucleic acid to form a complex;

(c) labelling the complex with a magnetic label;

(d) releasing the complex from the support; and (e) sorting the released chromosomes by means of said magnetic label.

30. The method according to claim 29 wherein said label is a magnetic particle having an average diameter from about 50 nm to about 2 microns.

31. The method according to claim 29 wherein said label further includes a fluorescent label.

* * * * *

UNITED STATES PATENT AND TRADEMARK OFFICE
CERTIFICATE OF CORRECTION

PATENT NO. : 5,508,164
DATED : April 16, 1996
INVENTOR(S) : Kausch et al.

It is certified that error appears in the above-identified patent and that said Letters Patent is hereby corrected as shown below:

<u>Title page,</u>
Item [73], please correct the assignee name after "Dekalb Genetics Corporation, Mystic, Conn." by inserting -- ; The Regents of the University of California, Oakland, CA --.

Signed and Sealed this

Twenty-second Day of October, 2002

Attest:

Attesting Officer

JAMES E. ROGAN
*Director of the United States Patent and Trademark Office*